United States Patent [19]
Jirtle et al.

[11] Patent Number: 5,874,222
[45] Date of Patent: Feb. 23, 1999

[54] M6P/IGF-II RECEPTOR TUMOR SUPPRESSOR GENE

[75] Inventors: Randy L. Jirtle, Durham, N.C.; Angus T. DeSouza, London, England; Gerald R. Hankins, Charlottesville, Va.

[73] Assignees: Duke University, Durham, N.C.; Zeneca Limited, London, England

[21] Appl. No.: 749,852

[22] Filed: Nov. 15, 1996

Related U.S. Application Data

[60] Provisional application No. 60/006,844 Mar. 16, 1995.

[51] Int. Cl.$^6$ .............................. C12Q 1/68; C07H 21/04
[52] U.S. Cl. .................................. 435/6; 436/64; 436/94; 536/23.5; 935/77; 935/78
[58] Field of Search .................................. 435/6; 436/64, 436/94; 935/77, 78; 536/23.5

[56] References Cited

PUBLICATIONS

Souza et al, "Microsatellite instability in the insulin–like growth factor II receptor gene in gastrointestinal tumours", nature genetics 14:255 (1996).
Jirtle, "9 Liver Tumor Promotion and Breast Cancer Chemoprevention: Common Mechanisms", Liver Tumor Promotion and Breast Cancer Chemoprevention, Ernst Schering Research Foundation, Workshop 10, Nongenotoxic Carcinogenesis, A. Cockburn, L. Smith eds., pp. 157–171 (1994).
Hankins et al, "The Role of Growth Factors in Liver Regeneration and Tumor Promotion", FASEB Journal, p. A1029, Abstract No. 538 (1992).
Jirtle et al, "Regulation of mannose 6–phosphate/insulin–like growth factor–II receptors and transforming growth factor beta during liver tumor promotion with phenobarbital", Carcinogenesis 15(8):1473–1478 (1994).
Sleat et al, "Increased Levels of Glycoproteins Containing Mannose 6–Phosphate in Human Breast Carcinomas", Cancer Research 55:3424–3430 (1995).
De Souza et al, "Imprinted genes in liver carcinogenesis", The FASEB Journal 11:60–67 (1997).
De Souza et al. Oncogene. 10:1725–1729, May 1995.
De Souza et al. FASEB Journal. 9(3): A124, Abstract #725, Mar. 1995.
De Souza et al, "M6P/IGF2R gene is mutated in human hepatocellular carcinomas with loss of heterozygosity", Nature Genetics 11:447–449 (1995).
Laurenzi et al, "The Expression of the Type II Insulin–Like Growth Factor Receptor (M6"/IGF–II Receptor) in a Human Glioblastoma–Derived Cell Line", Neuroscience Research Communications 16(1):37–43 (1995).
Ellis et al, "Affinity for the Insulin–Like Growth Factor–II (IGF–II) Receptor Inhibits Autocrine IGF–II Activity in MCF–7 Breast Cancer Cells", Molecular Endocrinology 10(3):286–297 (1996).
Hankins et al, "M6P/IGF2 receptor: a candidate breast tumor suppressor gene", Oncogene 12(9):2003–2009 (1996).
De Souza et al, "Frequent loss of heterozygosity on 6q at the mannose 6–phosphate/insulin–like growth factor II receptor locus in human hepatocellular tumors", Oncogene 10(9):1725–1729 (1995).
Xu et al, "Aberrant imprinting of the insulin–like growth factor II receptor gene in Wilms' tumor", Oncogene 14(9):1041–1046 (1997).

*Primary Examiner*—Carla J. Myers
*Attorney, Agent, or Firm*—Nixon & Vanderhye P.C.

[57] ABSTRACT

The present invention relates, in general, to a tumor suppressor and, in particular, to the mannose 6-phosphate/insulin-like growth factor-II (M6P/IGF-II) receptor and to diagnostic and therapeutic approaches based on same.

20 Claims, 11 Drawing Sheets

Fig. 2A
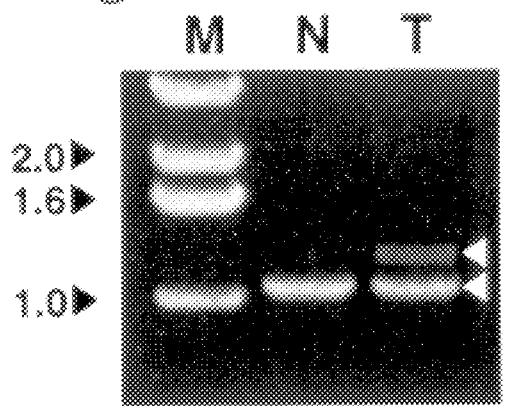
Fig. 2B
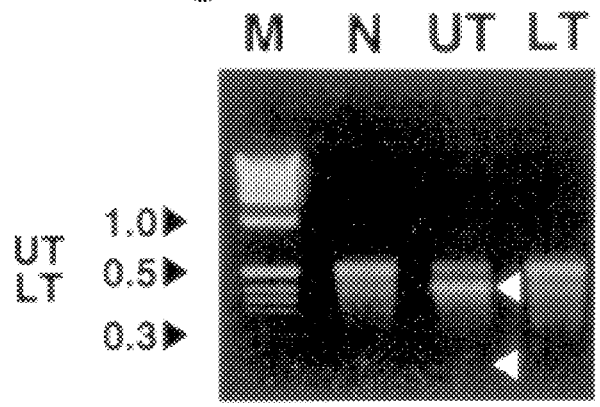
Fig. 2C
```
N  CCACAACGGAGTCTC---------------------------------   6215
T  CCACAACGGAGTCTCgtgagtgccttcccagtcacccgcggcgcacac   6250
     H  N  G  V  S  *
N  ------------------------------------------------
T  cctcagcatgtgaacttcagactgcttgacgatggttggctcttttggt   6300
N  ------------------------------------------------
T  tctcaagatgggaatactatgcccatgtgaggctgatggtggttgagttg   6350
N  ------------------------------------------------
T  tgactgttcctggaagcagccgcagtgtcaatctggcacagagggtgg    6400
N  --------GTACTATATAAATCTGTG                         6233
T  ctctgagGTACTATATAAATCTGTG                          6425
```

Fig. 3A
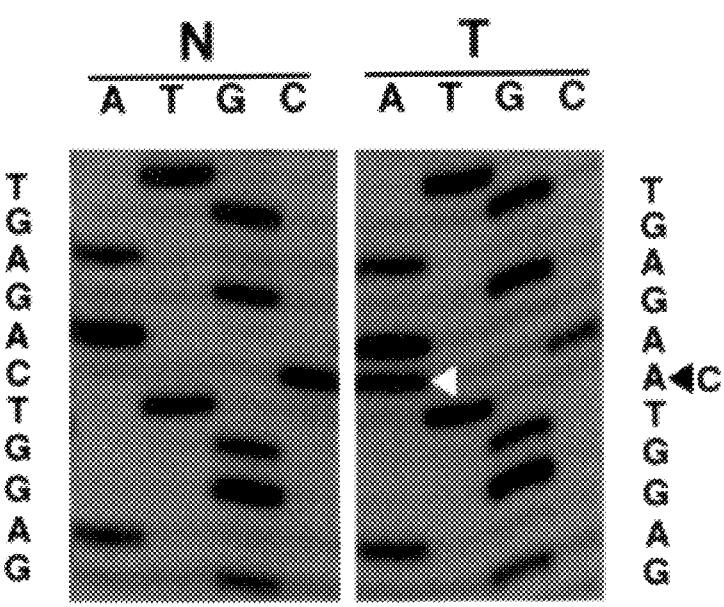
Fig. 3B
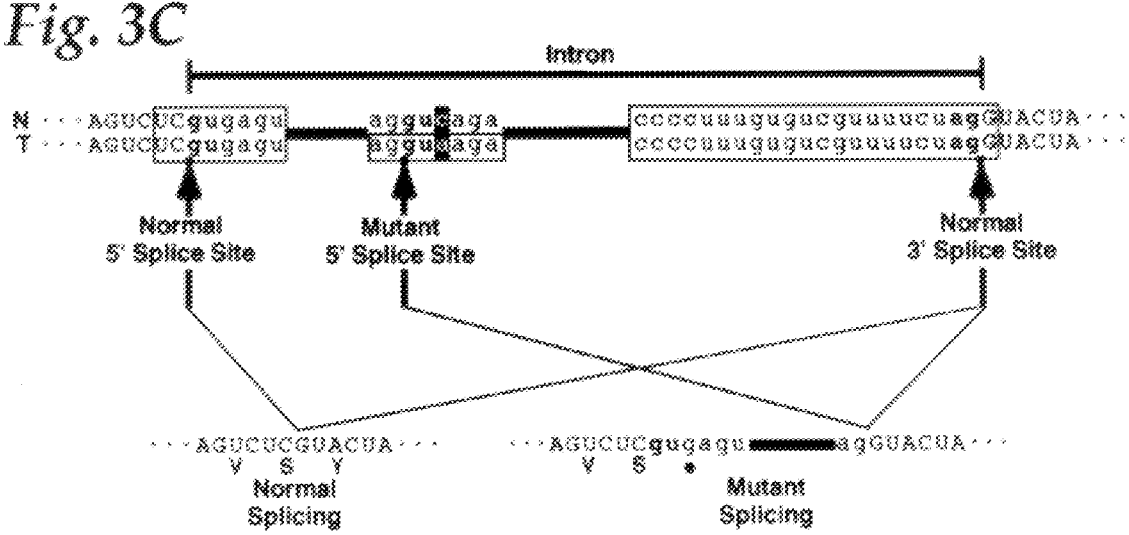
Fig. 3C

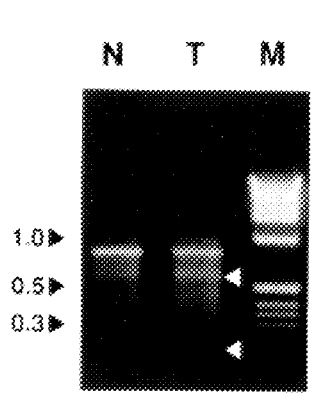
*Fig. 7A*
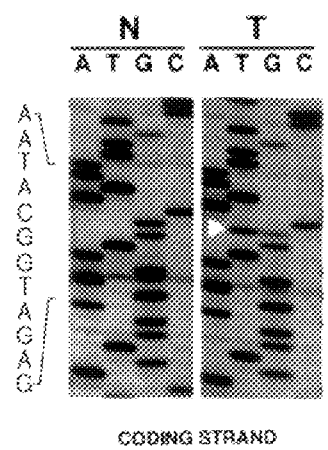
*Fig. 7B*
CODING STRAND
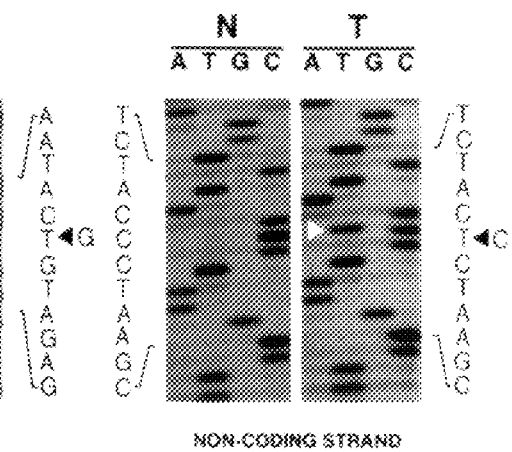
*Fig. 7C*
NON-CODING STRAND
*Fig. 7D*

N AACCTCGGCAGGGTAAGGGACCTGAGTGGAGAGATGGCATAATTGTCCTGAAATAC 4512
  N  L  G  R  V  R  D  G  P  Q  W  R  D  G  I  I  V  L  K  Y  1455

T AACCTCGGCAGGGTAAGGGACCTCATTGGAGAGATGGCATAATTGTCCTGAAATAC 4512
  N  L  G  R  V  R  D  G  P  H  W  R  D  G  I  I  V  L  K  Y  1455

*Fig. 9B*

Fig. 10A
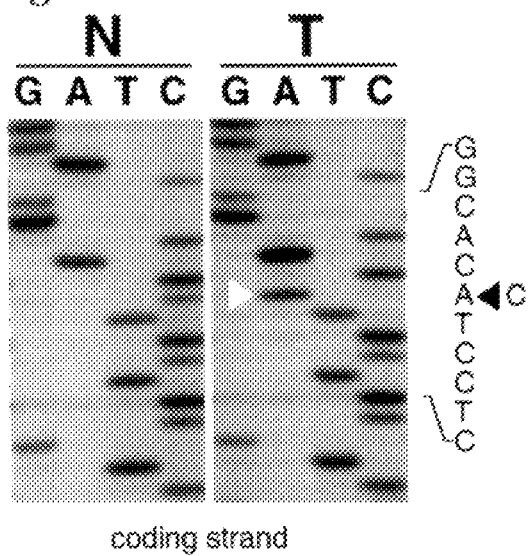
coding strand
Fig. 10B
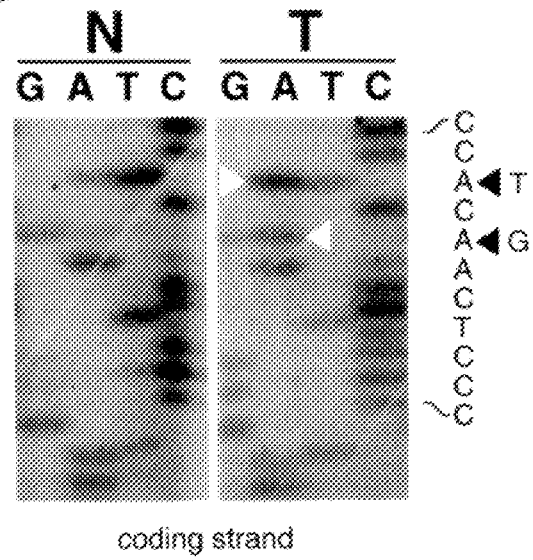
coding strand
Fig. 10C

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAACTTCTCC TACAGCAAGT GG                        22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AAACAAAAGT TGTCTGCCCT CC                        22

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAGCTTACTT ATCACTGTTT CC                        22

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:4:

GATAATACGA CTCACTATAG GGCCCTCCAA AGAAGTTGGA GTGC 44

(2) INFORMATION FOR SEQ ID NO:5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

TCATTTAGGT GACACTATAG GAGTAGTTGT CCCCATTGGT CCTC 44

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

GTCCCAGGAC CTGGACGTCA CC 22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:7:

TGTGACTGTT CCTGGAAGCA GC 22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:8:

CAGGTTCTTC CAGCTCCAGA GG 22

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:9:

CGTGCATGGG ATTTAGTGGC TGAC 24

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TGGAAGGGGA CAACTGTGAG G 21

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:11:

ACCACCAGTG CGATGAATAA GGG 23

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GATAATACGA CTCACTATAG GGCTGGCAAC TCCTTCGACC TC 42

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:13:

TCATTTAGGT GACACTATAG GACAGTGCGA TGAATAAGGG GAGAC 45

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:14:

GCCGTGCCCT CCAGAAGCAG CC                                                                          22

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:15:

CACTTGGCTC TCGCTGCAGG TG                                                                          22

( 2 ) INFORMATION FOR SEQ ID NO:16:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:16:

CCAGAAGCAG CCGCGTGTCT GC                                                                          22

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TCGCTGCAGG TGAATCGGAT GG                                                                          22

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:18:

AAACAAAAGT TGTCTGCCCT CC                                                                          22

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

(v) FRAGMENT TYPE: linear (xi) SEQUENCE DESCRIPTION: SEQ ID NO:19:

GTCCCAGGAC CTGGACGTCA CC    22

(2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:20:

GATAATACGA CTCACTATAG GGCCCTCCAA AGAAGTTGGA GTGC    44

(2) INFORMATION FOR SEQ ID NO:21:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:21:

TCATTTAGGT GACACTATAG GACAGTCCGC CCAGGTTCTT CCAG    44

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:22:

GCCGTGCCCT CCAGAAGCAG CC    22

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:23:

CACTTGGCTC TCGCTGCAGG TG    22

(2) INFORMATION FOR SEQ ID NO:24:

(i) SEQUENCE CHARACTERISTICS:
        (A) LENGTH: 22 base pairs
        (B) TYPE: nucleic acid ( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:24:

CCAGAAGCAG CCGCGTGTCT GC 22

( 2 ) INFORMATION FOR SEQ ID NO:25:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:25:

TCGCTGCAGG TGAATCGGAT GG 22

( 2 ) INFORMATION FOR SEQ ID NO:26:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:26:

GTGAATAAGG AAGAAGAGAC AG 22

( 2 ) INFORMATION FOR SEQ ID NO:27:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:27:

TTATTTGGTT GGAGGTGCTT GG 22

( 2 ) INFORMATION FOR SEQ ID NO:28:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:28:

GTGAATAAGG AAGAAGAGAC AG 22

( 2 ) INFORMATION FOR SEQ ID NO:29:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:29:

```
CACTGGGTGG GAGCTCTCTG CC                                              22
```

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:30:

```
GATGACCAGG ACAGTGAGGA TGAG                                            24
```

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:31:

```
TTCCCTTTCC TCGCCTTCTC AC                                              22
```

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:32:

```
ACCCAGTGAG AAACGCACAG AG                                              22
```

( 2 ) INFORMATION FOR SEQ ID NO:33:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:33:

TTATTTGGTT GGAGGTGCTT GG 22

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:34:

CCACAACGGA GTCTC 15

( 2 ) INFORMATION FOR SEQ ID NO:35:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:35:

CCACAACGGA GTCTCGTGAG TGCCTTCCCA GTCCACCCGC GGCGCCACAC 50

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: linear ( x i ) SEQUENCE DESCRIPTION: SEQ ID NO:36:

His Asn Gly Val Ser
1                        5

( 2 ) INFORMATION FOR SEQ ID NO:37:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:37:

CCTCAGCATG TGAACTTCAG ACTGCTTGAC GATGGTTGGC TCTTTTGGGT 50

( 2 ) INFORMATION FOR SEQ ID NO:38:

( i ) SEQUENCE CHARACTERISTICS:
        ( A ) LENGTH: 50 base pairs
        ( B ) TYPE: nucleic acid
        ( C ) STRANDEDNESS: single (D) TOPOLOGY: linear (ii) MOLECULE TYPE: DNA (genomic)

(v) FRAGMENT TYPE: linear (xi) SEQUENCE DESCRIPTION: SEQ ID NO:38:

TCTCAAGATG GGAATACTAT GCCCATGTGA GGCTGATGGT GGTTGAGTTG  50

(2) INFORMATION FOR SEQ ID NO:39:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(v) FRAGMENT TYPE: linear (xi) SEQUENCE DESCRIPTION: SEQ ID NO:39:

TGACTGTTCC TGGAAGCAGC CCGCAGTGTC AATCCTGGCA CAGAGGGTGG  50

(2) INFORMATION FOR SEQ ID NO:40:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(v) FRAGMENT TYPE: linear (xi) SEQUENCE DESCRIPTION: SEQ ID NO:40:

GTACTATATA AATCTGTG  18

(2) INFORMATION FOR SEQ ID NO:41:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(v) FRAGMENT TYPE: linear (xi) SEQUENCE DESCRIPTION: SEQ ID NO:41:

TTCTGAGGTA CTATATAAAT CTGTG  25

(2) INFORMATION FOR SEQ ID NO:42:

(i) SEQUENCE CHARACTERISTICS:
(A) LENGTH: 250 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:42:

CCACAACGGA GTCTCGTGAG TGCCTTCCCA GTCCACCCGC GGCGCCACAC CCTCAGCATG  60

TGAACTTCAG ACTGCTTGAC GATGGTTGGC TCTTTTGGGT TCTCAAGATG GGAATACTAT  120

GCCCATGTGA GGCTGATGGT GGTTGAGTTG TGACTGTTCC TGGAAGCAGC CCGCAGTGTC  180

| | | | | | |
|---|---|---|---|---|---|
| AATCCTGGCA | CAGAGGGTGG | TTCTGAGGTC | AGAGTGGGGG | CAGGAGCTTT | GGTGACTGGA | 240
| AACGGAGCCT | | | | | 250

(2) INFORMATION FOR SEQ ID NO:43:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:43:

| | | | | | |
|---|---|---|---|---|---|
| CCACAACGGA | GTCTCGTGAG | TGCCTTCCCA | GTCCACCCGC | GGCGCCACAC | CCTCAGCATG | 60
| TGAACTTCAG | ACTGCTTGAC | GATGGTTGGC | TCTTTTGGGT | TCTCAAGATG | GGAATACTAT | 120
| GCCCATGTGA | GGCTGATGGT | GGTTGAGTTG | TGACTGTTCC | TGGAAGCAGC | CCGCAGTGTC | 180
| AATCCTGGCA | CAGAGGGTGG | TTCTGAGGTA | AGAGTGGGGG | CAGGAGCTTT | GGTGACTGGA | 240
| AACGGAGCCT | | | | | 250

(2) INFORMATION FOR SEQ ID NO:44:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (genomic)

(v) FRAGMENT TYPE: linear (xi) SEQUENCE DESCRIPTION: SEQ ID NO:44:

AGUCUCGUGA GU              12

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: RNA (genomic)

(v) FRAGMENT TYPE: linear (xi) SEQUENCE DESCRIPTION: SEQ ID NO:45:

CCCCUUUGUG UCGUUUUCUA GGUACUA      27

(2) INFORMATION FOR SEQ ID NO:46:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (genomic)

(v) FRAGMENT TYPE: linear (xi) SEQUENCE DESCRIPTION: SEQ ID NO:46:

AGUCUCGUAC UA             12

( 2 ) INFORMATION FOR SEQ ID NO:47:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA (genomic)

( v ) FRAGMENT TYPE: linear ( x i ) SEQUENCE DESCRIPTION: SEQ ID NO:47:

```
AGUCUCGUGA GU                                                              12
```

( 2 ) INFORMATION FOR SEQ ID NO:48:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:48:

```
CCTCAGTGGA GAGATGGCAT AATTGTCCTG AAATACGTTG ATGGCGACTT ATGTCCAGAT          60
GGGATTCGGA AA                                                              72
```

( 2 ) INFORMATION FOR SEQ ID NO:49:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: linear ( x i ) SEQUENCE DESCRIPTION: SEQ ID NO:49:

```
Pro Gln Trp Arg Asp Gly Ile Ile Val Leu Lys Tyr Val Asp Gly Asp
 1               5                  10                  15
Leu Cys Pro Asp Gly Ile Arg Lys
                20
```

( 2 ) INFORMATION FOR SEQ ID NO:50:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:50:

```
CCTCAGTGGA GAGATGTCAT AATTGTCCTG AAATACGTTG ATGGCGACTT ATGTCCAGAT          60
GAGGATTCGG AAA                                                             73
```

( 2 ) INFORMATION FOR SEQ ID NO:51:

( i ) SEQUENCE CHARACTERISTICS:

(A) LENGTH: 24 amino acids
(B) TYPE: amino acid
(C) STRANDEDNESS:
(D) TOPOLOGY: linear (ii) MOLECULE TYPE: peptide (v) FRAGMENT TYPE: linear (xi) SEQUENCE DESCRIPTION: SEQ ID NO:51:

```
Pro Gln Trp Arg Asp Val Ile Ile Val Leu Lys Tyr Val Asp Gly Asp
1               5                   10                  15

Leu Cys Pro Asp Glu Ile Arg Lys
            20
```

(2) INFORMATION FOR SEQ ID NO:52:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (genomic)

(v) FRAGMENT TYPE: linear (xi) SEQUENCE DESCRIPTION: SEQ ID NO:52:

AACCTCGGCA GGGTAAGGGA CGGACCTCAG TGGAGAGATG GCATAATTGT CCTGAAATAC    60

(2) INFORMATION FOR SEQ ID NO:53:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (v) FRAGMENT TYPE: linear (xi) SEQUENCE DESCRIPTION: SEQ ID NO:53:

```
Asn Leu Gly Arg Val Arg Asp Gly Pro Gln Trp Arg Asp Gly Ile Ile
1               5                   10                  15

Val Leu Lys Tyr
            20
```

(2) INFORMATION FOR SEQ ID NO:54:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (genomic)

(v) FRAGMENT TYPE: linear (xi) SEQUENCE DESCRIPTION: SEQ ID NO:54:

AACCTCGGCA GGGTAAGGGA CGGACCTCAT TGGAGAGATG GCATAATTGT CCTGAAATAC    60

(2) INFORMATION FOR SEQ ID NO:55:

(i) SEQUENCE CHARACTERISTICS:
(A) LENGTH: 20 amino acids
(B) TYPE: amino acid
(C) STRANDEDNESS:
(D) TOPOLOGY: linear ( i i ) MOLECULE TYPE: peptide ( v ) FRAGMENT TYPE: linear ( x i ) SEQUENCE DESCRIPTION: SEQ ID NO:55:

Asn Leu Gly Arg Val Arg Asp Gly Pro His Trp Arg Asp Gly Ile Ile
1               5                   10                  15

Val Leu Lys Tyr
            20

( 2 ) INFORMATION FOR SEQ ID NO:56:

( i ) SEQUENCE CHARACTERISTICS:
( A ) LENGTH: 78 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:56:

CCTCCTCCAC GGCAGGGAAA GGAAGGGCAG GAGAACGGCC ATATTACCAC CAAGTCAGTG            60

AAAGCCCTCA GCTCCCTG                                                         78

( 2 ) INFORMATION FOR SEQ ID NO:57:

( i ) SEQUENCE CHARACTERISTICS:
( A ) LENGTH: 26 amino acids
( B ) TYPE: amino acid
( C ) STRANDEDNESS:
( D ) TOPOLOGY: linear ( i i ) MOLECULE TYPE: peptide ( v ) FRAGMENT TYPE: linear ( x i ) SEQUENCE DESCRIPTION: SEQ ID NO:57:

Pro Pro Pro Arg Gln Gly Lys Glu Gly Gln Glu Asn Gly His Ile Thr
1               5                   10                  15

Thr Lys Ser Val Lys Ala Leu Ser Ser Leu
            20                  25

( 2 ) INFORMATION FOR SEQ ID NO:58:

( i ) SEQUENCE CHARACTERISTICS:
( A ) LENGTH: 78 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:58:

CCTCCTACAC GGCAGGGAAA GGAAGGGCAG GAGAACGGCC ATATTACCAC CAAGTCAGTG            60

AAAGCCCTCA ACACCCTG                                                         78

( 2 ) INFORMATION FOR SEQ ID NO:59:

( i ) SEQUENCE CHARACTERISTICS:
( A ) LENGTH: 26 amino acids
( B ) TYPE: amino acid
( C ) STRANDEDNESS:
( D ) TOPOLOGY: linear (i i) MOLECULE TYPE: peptide (v) FRAGMENT TYPE: linear (x i) SEQUENCE DESCRIPTION: SEQ ID NO:59:

```
Pro Pro Thr Arg Gln Gly Lys Glu Gly Gln Glu Asn Gly His Ile Thr
1               5                   10                  15
Thr Lys Ser Val Lys Ala Leu Asn Thr Leu
            20                  25
```

M6P/IGF-II RECEPTOR TUMOR SUPPRESSOR GENE

This application is based on and claims priority from Provisional Application Ser. No. 60/006,844, filed Nov. 16, 1995.

TECHNICAL FIELD

The present invention relates, in general, to a tumor suppressor and, in particular, to the mannose 6-phosphate/insulin-like growth factor-II (M6P/IGF-II) receptor and to diagnostic and therapeutic approaches based on same.

BACKGROUND

The study of genetic lesions such as tumor-associated deletions has led to the identification of a number of tumor-suppressor genes which, if deleted or mutated, relieve the cell from negative growth control (Ponder, Nature 335:400 (1988); Stanbridge, Annu. Rev. Genet. 24:615 (1990); Lasko et al, Annu. Rev. Genet. 25:281 (1991); Marshall, Cell 64:313 (1991)). An inactivating mutation in one allele of a tumor suppressor gene is recessive, but becomes evident when the other allele is lost. This second event is often signified by loss of heterozygosity (LOH) at polymorphic DNA marker loci in or near the gene. LOH in human hepatocellular carcinomas (HCCs) has been observed on a number of chromosomal arms including 4q, 5q, 8p, 10q, 11p, 13q, 16q, 17p and 22q (Wang and Rogler, Cytogenet. Cell Genet. 48:72 (1988); Buetow et al, Proc. Natl. Acad. Sci. USA 86:8852 (1989); Tsuda et al, Proc. Natl. Acad. Sci. USA 87:6791 (1990); Zhang et al, Jpn. J. Cancer Res. 81:108 (1990); Fujimori et al, Cancer Res. 51:89 (1991); Walker et al, Cancer Res. 51:4367 (1991); Emi et al, Cancer Res. 52:5368 (1992); Nose et al, Cancer 72:355 (1993), Takahashi et al, Hepatology 17:794 (1993)).

Expression of the mannose 6-phosphate/insulin-like growth factor II (M6P/IGF-II) receptor is often significantly reduced in both rat (Jirtle et al, Carcinogenesis 15:1473 (1994)) and human (Sue et al, Ann. Surgery, 222:171 (1995)) HCCs. The M6P/IGF-II receptor possesses distinct binding regions for both phosphomannosyl residues and IGFII (MacDonald et al, Science 239:1134 (1988); Kornfeld, Annu. Rev. Biochem. 61:307 (1992)). Primary functions of the M6P/IGF-II receptor include the trafficking of newly synthesized lysosomal enzymes from the Golgi to the lysosomes, and the endocytosis of extracellular lysosomal enzymes (Dahms et al, J. Biol. Chem. 264:12115 (1989)). However, apart from IGFII, secreted growth factors like proliferin (Lee and Nathans, J. Biol. Chem. 263:3521 (1988)) and the latent complex of TGFβ1 (Purchio et al, J. Biol. Chem. 263:14211 (1988); Kovacina et al, Biochem. Biophys. Res. Commun. 160:393 (1989)) also bind to the M6P/IGF-II receptor. Although binding of these growth factors to the M6P/IGF-II receptor will lead to their internalization and subsequent degradation in the lysosomes, the extracellular activation of TGFβ1 by plasmin is also greatly facilitated by the binding of the TGFβ latent complex to this receptor (Dennis and Rifkin, Proc. Natl. Acad. Sci. USA 88:580 (1991), Le Bleser et al, Hepatology 21:1429 (1995)), Kojima et al, J. Cell Biol. 121:439 (1993)). The M6P/IGF-II receptor is therefore required for both the activation of the growth inhibitor, TGFβ1 (Dennis and Rifkin, Proc. Natl. Acad. Sci. USA 88:580 (1991)) and the degradation of the mitogen, IGFII (Morgan et al, Nature 329:301 (1987); Kornfeld, Annu. Rev. Biochem. 61:307 (1992)). Consequently, the M6P/IGF-II receptor also plays an important role in negative cell growth control.

LOH at the M6P/IGF-II receptor locus in HCCs was recently reported (DeSouza et al, Oncogene 10:1725 (1995)). The presence of LOH in adenomas was also described, suggesting that allelic loss may be an early event in the etiology of hepatocellular tumors.

SUMMARY OF THE INVENTION

The present invention relates to the M6P/IGF-II receptor and to mutant forms thereof, particularly, those forms observed in tumors, including hepatocellular and breast tumors. The invention further relates to methods of tumor detection and diagnosis and to new modes of cancer therapy.

Further objects and advantages of the present invention will be clear from the description that follows.

BRIEF DESCRIPTION OF THE DRAWINGS

FIGS. 2A–C Insertion mutation in the M6P/IGF-II receptor mRNA from a hepatocellular carcinoma (HCC) with LOH. (A)—RT-PCR products from surrounding normal (N) and tumor (T) tissues. The upper tumor (UT) band was approximately 200 bp larger than expected whereas the lower tumor (LT) band co-migrated with the normal band (SEQ ID NO:34, SEQ ID NO:35, SEQ ID NO:36, SEQ ID NO:37, SEQ ID NO:38, SEQ ID NO:39, SEQ ID NO:40, and SEQ ID NO:41). (B)—Mismatch detection between normal (N) and tumor (UT and LT) cDNA templates using T7 and SP6 transcripts, respectively. Only the UT derived template produced RNase A cleavage bands (white triangles) different from the control (N). In both (A) and (B), the marker (M) was a 1 kilobase pair DNA ladder (GIBCO BRL, Gaithersburg, Md.). (C)—cDNA sequence of a 192 bp insert (lower case) in M6P/IGF-II receptor mRNA from the tumor. The numbers indicate the position of the insert within the full length transcript. Amino acids are positioned in the center of each codon and the stop codon is highlighted in bold type.

FIGS. 3A–C Mutant intron splicing in a HCC with LOH. (A)—Sequence for the 5' end of the intron (intron 40 based on the mouse gene (Szebenyi et al, Genomics 19:120 (1994)) from genomic DNA (SEQ ID NO:42 and SEQ ID NO:43). Exon and intron sequences are shown in upper and lower case, respectively. The C:G→A:T transversion is highlighted with a black box. Box A is the normally used 5' splice site and Box B is the mutant 5' splice site in the tumor. The numbers indicate the postion of the intron within the full length M6P/IGF-II receptor mRNA transcript. (B)—Direct sequencing (coding strand) of intron DNA amplified from genomic DNA showing the C:G→A:T transversion (white triangle) in tumor. The mutant and surrounding normal DNAs were sequenced in both directions. Contaminating normal DNA (De Souza et al, Oncogene 10:1725 (1995)) is observed at the mutant locus as a co-migrating band. (C)—Proposed model for intron splicing in tumor. 5' and 3' splice sites are shown boxed (SEQ ID NO:44, SEQ ID NO:45, SEQ ID NO:46, and SEQ ID NO:47). The gu and ag dinucleotides present on the 5' and 3' boundaries of introns are highlighted in bold type (Horowitz et al, Trends Genet. 10:100 (1994), Padgett et al, Ann. Rev. Biochem. 55:1119 (1986)). The C:G→A:T transversion is highlighted with a black box. Mutant splicing results in the 5' end of this intron remaining in mature M6P/IGF-II receptor message.

FIGS. 7A–D Point mutations in the M6P/IGF2-II receptor gene in HCCs with LOH. (A)—Mismatch detection for the G:C→T:A transversion between normal (N) and tumor (T) cDNA templates using T7 and SP6 transcripts, respectively (see FIG. 2 above). The tumor derived template produced two RNase A cleavage bands (white triangles). The marker (M) was a 1 kbp DNA ladder (GIBCO BRL, Gaithersburg, Md.). (B)—Direct sequencing (coding strand) of PCR template derived from genomic DNA showing the G:C→T:A transversion (white triangle). (C)—Direct sequencing (non-coding strand) of PCR template derived from genomic DNA showing the G:C→A:T transition (white triangle). In both (B) and (C), the mutants and their surrounding normal DNAs were sequenced in both directions. Contaminating normal DNA (De Souza, Oncogene 10:1725 (1995)) is observed at the mutant locus as a co-migrating band. (D)—Changes at the DNA and protein levels for the two mutations (SEQ ID NO:48, SEQ ID NO:49, SEQ ID NO:50, and SEQ ID NO:51). Mutant loci are highlighted with a black box. The G:C→T:A transversion substitutes a Val for Gly$^{1449}$, and the G:C→A:T transition substitutes a Glu for Gly$^{1464}$. Amino acids underlined are conserved among human, bovine, rat and mouse (alignment was done using the Higgins-Sharp algorithm, MacDNASIS® Pro v3.2, Hitachi Software Engineering America, Ltd).

FIGS. 9A–B Point mutation in exon 31 (based on the mouse gene) in a carcinoma in situ with LOH. A, Direct sequencing (non-coding strand) of PCR template derived from genomic DNA showing the G:C→T:A transversion (white triangle). Both the mutant and their surrounding normal DNAs were sequenced in both directions (coding strand not shown). Contaminating normal DNA is observed at the mutant locus as a co-migrating band. B, Changes at the DNA and protein levels (SEQ ID NO:52, SEQ ID NO:53, SEQ ID NO:54, and SEQ ID NO:55). Amino acids which are conserved among human, mouse, rat and bovine are underlined.

FIGS. 10A–C Point mutations in exon 48 (based on the mouse gene) in a carcinoma in situ and an invasive carcinoma, both with LOH. A, Direct sequencing (coding strand) of PCR template derived from genomic DNA showing the C:G→A:T transversion in the carcinoma in situ (white triangle). B, Direct sequencing (coding strand) of PCR template derived from genomic DNA showing the G:C→A:T transition and T:A→A:T transversion in the invasive carcinoma (white triangles). In each case, both the mutant and their surrounding normal DNAs were sequenced in both directions (non-coding strand not shown). Contaminating normal DNA is observed at the mutant locus as a co-migrating band. C, Changes at the DNA and protein levels (SEQ ID NO:56, SEQ ID NO:57, SEQ ID NO:58, and SEQ ID NO:59). Amino acids which are conserved among human, mouse, rat and bovine are underlined. Residues also conserved in the MARCKS family proteins and MRP are indicated by a double underline.

DETAILED DESCRIPTION OF THE INVENTION

Figure 1:
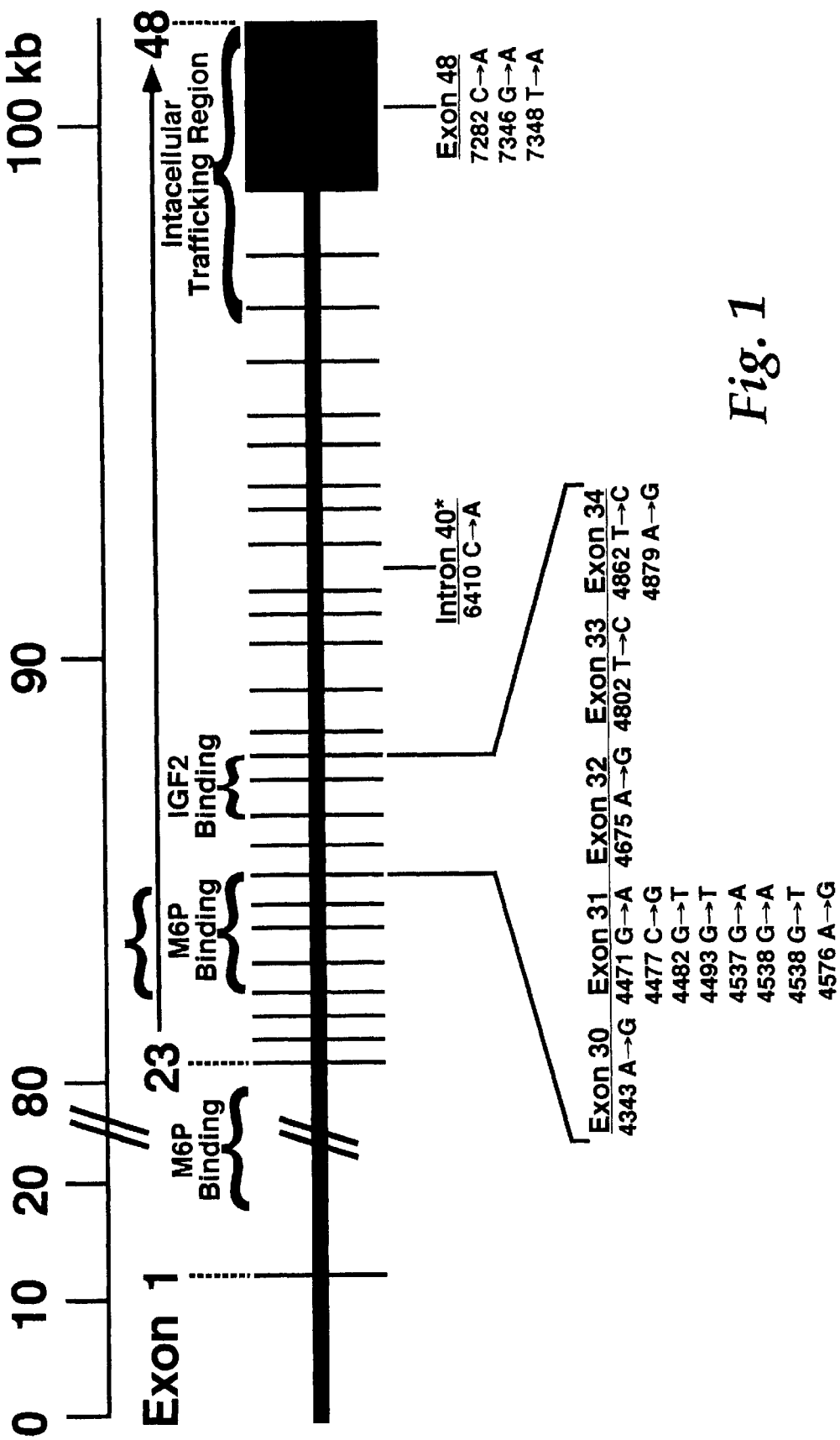
FIG. 1 Mutations identified in HCC and breast tumors and their gene locations.

The present invention is based, at least in part, on the demonstration that the M6P/IGF-II receptor functions as a tumor suppressor. The tumor suppressive activity of this receptor was suggested by studies demonstrating a frequent LOH at the M6P/IGF-II receptor locus in hepatocellular tumors (De Souza et al, Oncogene 10:1725 (1995)). Mutations in the M6P/IGF-II receptor gene in HCCs and breast tumors with LOH (squamous cell carcinomas also having LOH at this gene locus) have now been identified.

In patients with liver cirrhosis and viral hepatitis infection, 61% of the hapatocellular carcinomas (HCCs) and 63% of the premalignant dyplastic liver lesions have been found to have LOH at the M6P/IGF-II receptor locus. Inactivating mutations have been found in the remaining allele of 55% of these lesions, including deletions in a poly-deoxyguanine tract recently shown to be a target of microsatellite instability in gastrointestinal tumors (Souza et al, Nature Genet. 14 Nov.:255 (1996)). LOH at this locus was even found in 60% of cirrhotic nodules, comprised of phenotypically normal hepatocytes, surrounding the developing HCCs and dysplastic lesions. These findings indicate that loss of the M6P/IGF-II receptor gene is an initating event in human liver carcinogenesis. The M6P/IGF-II receptor is commonly lost at an early stage of human breast tumorigenesis (Hankins et al, Oncogene 12:2003 (1990)). Like the TGFβ type II receptor (Markowitz et al, Science 268:1336 (1995)), the M6P/IGF-II receptor gene has also been shown to be a target of microsatellite instablity in replication/repair error-positive (RER+), but not RER−, human gastrointestinal tumors (Souza et al, Nature Genet. 14 Nov.:255 (1996)). This study indicates that the M6P/IGF-II receptor and TGFβ type II receptor are part of the same tumorigenesis pathway since mutation of either receptor, but not both, occurred in 90% of these RER+ tumors.

The human M6P/IGF-II receptor gene maps to 6q26–q27 (Laureys et al, Genomics 3:224 (1988)). Chromosomal deletions and LOH in markers in this region have been observed in certain tumor types, including breast cancer (Dutrillaux et al, Cancer Genet. Cytogenet. 49:203 (1990); Mars and Saunders, Cancer Met. Rev. 9:35 (1990); Devilee et al, Oncogene 6:1705 (1991)), ovarian carcinoma (Lee et al, Cancer Res. 50:2724 (1990); Saito et al, Cancer Res. 52:5815 (1992); Foulkes et al, Br. J. Cancer 67:551 (1993)), malignant melanoma (Millikin et al, Cancer Res. 51:5449 (1991)), lymphoma (Gaidano et al, Blood 80:1781 (1992)) and renal cell carcinoma (Morita et al, Cancer Res. 51:5817

(1991)), suggesting the presence of a putative tumor suppressor gene at this chromosomal location. However, chromosome 6 has not previously been shown to be a hot spot for allelic loss in HCCs. Mere LOH, however, in no way implicates the M6P/IGF-II receptor gene directly as the deleted region would contain many genes. The identification of point mutations in the remaining allele, as shown in the Examples that follow, presents evidence for the first time that this gene is functioning as a tumor supressor.

The data presented in the Examples that follow demonstrate that in tumors with LOH, mutations are present in the remaining allele. These mutations give rise, for example, to a truncated receptor protein and significant amino acid substitutions. Specifically, a C:G→A:T transversion has been detected in the genome of an HCC that results in the production of a truncated receptor lacking the transmembrane domain and lysosomal trafficking signal; a G:C→T:A transversion has been detected in the genome of a HCC that results in the substitution of Val for Gly$^{1449}$; and a G:C→A:T transition has been detected in a HCC that results in the substitution of Glu for Gly$^{1464}$. As for breast tumors, a G:C→T:A transversion has been identified in a comedo carcinoma in situ that results in a substitution of His for Gln$^{1445}$. A C:G→A:T transversion has been identified in a comedo carcinoma in situ that results in the substitution of Thr for Pro$^{2379}$. A G:C→A:T transition and a T:A→A:T transversion have been identified in an invasive carcinoma. These mutations result in the substitution of an Asn for Ser$^{2400}$ and a Thr for Ser$^{2401}$, respectively. All of the mutations thus far identified in HCCs and breast tumors and their gene location are shown in FIG. 1. The existence of mutant forms of the receptor makes possible various methods of tumor detection and diagnosis and the demonstration that the M6P/IGF-II receptor is a tumor suppressor provides new modes of cancer therapy.

Detection/Diagnosis:

The present invention includes within its scope methods for detecting/diagnosing in a subject a neoplastic or preneoplastic condition. Examples of conditions (eg tumors or tumourous tissue or preneoplastic tissue) that can be detected/ diagnosed in accordance with these methods include but are not limited to lung tumors (eg squamous cell carcinomas), ovarian tumors, prostate tumors, bladder tumors, pancreatic tumors, colorectal tumors, liver tumors (particularly hepatocellular carcinomas), and mammary tumors.

A first such method involves the use of genetic diagnostic techniques. For example, general mutation screening of the M6P/IGF-II receptor gene of a subject can be performed by such methods as direct sequencing or mismatch detection (see generally Naylor et al, Human Molec. Genet. 2:11 (1993); Giannelli, Bailliere's Clinical Haematology 2/4:821 (1989); Green et al, Amer. J. Human Genet. 45(4 Suppl): A191 (1989); Dundar et al, J. Medical Genet. 32:154 (1995)) or single strand conformation polymorphism (SSCP)(Orita et al, Proc. Natl. Acad. Sci. USA 86:2766 (1989), Orita et al, Genomics 5:874 (1989), Ainsworth et al, Methods Molec. Biol. 31:205 (1994), Beier, Mammalian Genome 4:627 (1993), Hayashi et al, Human Mutation 2:338 (1993), Fan et al, Mutation Research 288:85 (1993), Hayashi, Genet. Anal. Tech. Appl. 9:73 (1992), Hayashi, PCR Methods and Applications 1:34 (1991)) or restriction fragment length polymorphism (RFLP) analysis (Boyle, ed. Current Protocols Human Genet. 1:2 (1994), Pourzand et al, Mutation Res. 288:113 (1993), Narayan, Ann. Clin. Lab. Sci. 21:291 (1991), Vineis et al, Int. J. Can. 47:26 (1991), Zijlstra et al, Prog. Clin. Biol. Res. 347:187 (1990)) after polymerase chain reaction (PCR) (Nollan et al, Scand. J. Clin. Lab. Invest. 221:116 (1995); Reischl et al, Molec. Biotech. 3:55 (1975); Gibbs, Curr. Opin. Biotech. 2:69 (1991); Arnheim, Genet. Engin. 12:115 (1990); Taylor et al, Curr. Opin. Biotech. 6:24 (1995)) or reverse transcription (RT)-PCR (Cane et al, Electroph. 16:329 (1995); Salmon, Diag. Molec. Path. 4:2 (1995); Holodnig, Clin. Lab. Med. 14:335 (1994); Briggs et ak, Sem. Nephr. 13:2 (1993)). Suitable methods for PCR amplification have been described (see, for example, PCR Technology: Principles and Applications for DNA Amplification, ed HA Erlich, Freeman Press, New York, N.Y. (1992); PCR Protocols: A Guide to Methods and Applications, eds. Innis, Gelfland; Snisky, and White, Academic Press, San Diego, Calif. (1990); Mattila et al, Nucleic Acids Res. 19:4967 (1991); Eckert et al, PCR Methods and Applciations 1:17 (1991); PCR eds. McPherson, Quirkes, and Taylor, IRL Press, Oxford; and U.S. Pat. No. 4,683,202). A further method for detection of genetic mutations is the amplification refractory mutation system (ARMS) described in EPO 0 332 435.

Alternatively, tissue samples (eg suspected tumorous tissue) from a subject can be screened for the mutant form of the M6P/IGF-II receptor by in situ hybridization (Zhao et al, Cancer Res. 53:2901 (1993), Uner et al, Hemat./Oncol. Clin. North America 8:771 (1994), Hopman et al, Molec. Biol. Rep. 19:31 (1994), Bentz et al, Leukemia 8:1447 (1994), Brown et al, J. Urology 152:1157 (1994), DeLellis, Human Path. 25:580 (1994)) and/or immunohistochemistry (Jirtle et al, Carcinogenesis 15:1473 (1994), Calonje et al, Hemat./Oncol. Clin. North America 9:657 (1995), Szymas, Folia Neuropathol. 32:209 (1994), Yu et al, Histochem. J. 24:121 (1992), Miettinen, Ann. of Med. 25:221 (1993), Callea et al, Liver 12(4 Pt 2):290 (1992), Rahman et al, Malaysian J. Path. 13:17 (1991)). For example, the intron mutation described in the Example can be screened for by in situ hybridization using the indicated 192 bp insert as a probe.

A further detection/diagnostic method comprises: (a) obtaining from the subject a biological sample, and (b) detecting the presence in the sample of a mutant M6P/IGF-II receptor. In accordance with this method, the presence in the sample of the mutant receptor indicates that the subject has a neoplastic or preneoplastic condition.

Biological samples suitable for use in this method include biological fluids such as serum, plasma, urine lung lavage fluid, ascites fluid, saliva and cerebrospinal fluid. Since the M6P/IGF-II receptor is normally present in the circulation (Causin et al, Biochem. J. 252:795 (1988)), plasma and/or serum samples are preferred. Tissue samples (eg slices) can also be used in the method of the invention, including samples derived from biopsies. Cell cultures or cell extracts derived, for example, from tissue, and fecal, blood and sputum samples can also be used.

The detection step of the present method can comprise:
  i) contacting the biological sample with a compound (eg a protein or an oligonucleotide) that forms a complex with the mutant receptor under conditions such that the complex can form; and
  ii) determining whether any such complex has formed.

The compound is preferably a binding protein, eg an antibody, polyclonal or monoclonal, or antigen binding fragment thereof or an oligonucleotide that binds to the mutated M6P IGF-II receptor with high affinity. Antibodies specific for mutant forms of the M6P/IGF-II receptor, including the mutant forms described in the Examples, can be produced using art recognized techniques. Oligonucleotides specific for mutant receptor forms can be identified, for example, according to the method of Gold, J. Biol. Chem. 270:13581 (1995).

The compound, which can be labelled with a detectable marker (eg fluorophore, chromophore or isotope, etc), can be attached to a solid support such as a bead, plate, filter, resin, etc.

Determination of formation of the complex can be effected by contacting the complex with a further compound (eg antibody) that specifically binds to the first compound (or complex). Like the first compound, the further compound can be attached to a solid support and can be labeled with a detectable marker.

A modification of the foregoing method involves the use of antibodies specific for the wild type (normal) form of the receptor. Using this approach, samples, eg tumor tissue samples, can be screened for the absence of the wild type receptor as indicated by a lack of antibody binding. The M6P/IGF-II receptor is present both within the cell and on the cell surface thus, tissue slices or cultured cells can be used as samples.

Tumors that lack functional M6P/IGF-II receptors can be expected to contain an increased concentration of unbound M6P-containing glycoproteins. Therefore, a further method of the invention involves the use of either calcium dependent or independent M6P receptors (Sleat et al, Cancer Res. 55:3424 (1995)), antibodies to M6P-containing glycoproteins, or other compounds that specifically bind M6P-containing glycoproteins, to detect an elevation in the cellular levels of unbound M6P-containing glycoproteins. Using this approach, samples, eg tumor tissues, can be screened for the absence of the wild type receptor by detecting an elevation in the amount of unbound M6P-containing glycoprotein present in the sample.

The identification of mutant M6P/IGF-II receptors in accordance with the present invention makes possible the identification of subjects that are likely to benefit from adjuvant therapy. For example, a biological sample from a post primary therapy subject (eg subject having undergone surgery) can be screened for the presence of circulating mutant M6P/IGF-II receptor, the presence of such receptor being indicative of residual tumor tissue. Similarly, tissue from the cut site of a surgically removed tumor can be examined for the presence of mutant receptor, the presence being indicative of incomplete removal of the tumor. The ability to identify such subjects makes it possible to tailor therapy to the needs of the particular subject. Subjects undergoing non-surgical therapy, eg chemotherapy, gene therapy or radiation therapy, can likewise be monitored, the presence in samples from such subjects of mutant receptors being indicative of the need for continued treatment. Staging of the disease is also contemplated, for example, by lymph node biopsy either with antibody or oligonucleotide specific for mutant protein or with nucleic acid mutation detection methodology. Disease staging may influence treatment regimes.

Quantative determination of receptor levels, for example, in plasma, can be used as an indicator of tumor size. Extent of disease involvement can also be assessed by quantitating mutant receptor levels (e.g., in plasma).

The mutant-receptor specific antibodies of the invention (e.g., antibodies to mutant forms of the receptor expressed on the cell surface) or mutant-receptor specific oligonucleotides can also be used in vivo to detect and locate tumors. For example, antibodies of the invention, specific for mutant forms of the M6P/IGF-II receptor and labeled with a detectable label, can be administered (eg by injection) to a subject suspected of bearing a tumor and the subject then scanned (using an appropriate device given the nature of the label) for the presence of localized antibody.

The present invention also relates to a kit that can be used in the detection of a mutant M6P/IGF-II receptor or autoantibodies thereto. The kit can comprise a compound that specifically binds the mutant receptor (eg binding protein (eg antibodies or binding fragments thereof (eg $F(ab')_2$ fragments)) or oligonucleotide) or isolated or purified receptor forms recognized by autoantibodies against the mutant receptor, for example, disposed within a container means. The kit can further comprise ancillary reagents, including buffers and the like.

Therapy:

The present invention contemplates the use in gene therapy regimens of DNA sequences encoding the M6P/IGF-II receptor, or tumor suppressive portions thereof (e.g., the M6P-binding regions (eg repeats 1–3 and 7–9) or the IGF-II binding region (eg repeat 11) (Schmidt et al of J. Biol. Chem. 270:1495 (1995)). The encoding sequences can be present in a construct which, when introduced into target cells, results in expression of the DNA sequence and production of the receptor. Target cells include tumor cells present, for example, in the lung, ovary, prostate, bladder, pancreas, colon, brain, liver or breast of a subject undergoing treatment.

For gene therapy to be practical, it is desirable to employ a DNA transfer method that: (1) directs the therapeutic sequence into specific target cell types (eg, neoplastic cells such as those described above, particularly HCC and breast tumors), (2) is highly efficient in mediating uptake of the therapeutic polynucleotide into the target cell population, and (3) is suited for use in vivo for therapeutic application.

Delivery of the M6P/IGF-II receptor gene (or portion thereof encoding a tumor suppressive polypeptide) can be effected using any of a variety of methodologies. The presently available methodologies may be divided into three major groups: transfection with a viral vector; fusion with a lipid; and cationic supported DNA introduction. Each of these techniques has advantages and disadvantages, so that the selection of which technique to use depends upon the particular situation and its demands.

The majority of the approved gene transfer trials in the United States rely on replication-defective retroviral vectors harboring the therapeutic polynucleotide sequence as part of the retroviral genome (Miller et al, Mol. Cel. Biol. 10:4239 (1990); Kolberg, J. NIH Res. 4:43 (1992); Cornetta et al, Hum. Gene. Ther. 2:215 (1991)). Advantages of retroviral vectors for gene therapy include the high efficiency of gene transfer into replicating cells, the precise integration of the transferred genes into cellular DNA, and the lack of further spread of the sequences after gene transduction. Retroviruses are particularly suitable for use where target cells are present in a body compartment, such as brain and liver or epithelial surfaces such as lung, bladder or colon. Since retroviruses infect only dividing cells, they have the advantage of being self-targeting to tumor cells within these environments. Disadvantages include the inability of retroval vectors to infect nondividing cells, the inherent inability to characterize completely the retroviral vectors used for gene transduction (retroviral vectors cannot be made synthetically but must be produced by infected cultured cells), the inability to target distinct cell types selectively, and the potential for undesirable insertional mutagenesis of the host cell genome.

Adenoviral vectors have also been described for use in human gene therapy (Rosenfeld et al, Cell 68:143 (1992)). Advantages of adenovirus vectors include their potential to carry larger insert polynucleotide sequences than retroviral vectors, very high viral titres, ability to infect nonreplicating cells, and suitability for infecting tissues in situ, especially in the lung. Disadvantages include the inclusion of adenovirus genes in the vectors which encode viral proteins that can be immunogenic or result in other adverse effects, and potential instability of gene expression due to unstable integration into chromosomal DNA.

Alternatively, adenoassociated viruses, which integrate, can also be used, as can other viral systems depending on the target site, or natural/engineered tissue tropism. In this regard, a further viral vector that has advantage for use in the present invention is hepatitis virus. Hepatitis virus may be preferred when liver is the target tissue.

Because of their inherent antigenicity, many gene therapy methods employing viral vectors may be ill-suited for multiple administrations, such as may sometimes be required to treat chronic diseases such as cancer.

Another gene transfer method suitable for use in humans is physical transfer of plasmid DNA in liposomes directly into tumor cells in situ. Unlike viral vectors that must be propagated in cultured cells, plasmid DNA can be purified to homogeneity thereby reducing the potential for pathogenic contamination. It may not be necessary for the exogenous DNA to stably integrate into the transduced cell, since transient expression may suffice to kill the target (eg tumor) cells. Liposome-mediated DNA transfer has been described by various investigators (Wang and Huang, Biochem. Biphys. Res. Commun. 147:980 (1987); Wang and Huang, Biochemistry 28:9508 (1989); Litzinger and Huang, Biochem. Biophys. Acta 1113:201 (1992); Gao and Huang, Biochem. Biophys. Res. Commun. 179:280 (1991); Felgner, WO 91/17424; WO 91/16024). Liposomal compositions, however, may not possess the specificity necessary to deliver the exogenous DNA to all target cell types and non-physiological pH conditions may be necessary to effect fusion.

Immunoliposomes have also been described as carriers of exogenous polynucleotides (Wang and Huang, Proc. Natl. Acad. Sci. USA 84:7851 (1987); Trubetskoy et al, Biochem. Biophys. Acta 1131:311 (1992)). Immunoliposomes can be expected to have improved cell type specificity as compared to liposomes due to the inclusion of specific antibodies that bind to surface antigens on target cell types. Since, antibodies can be cross-reactive and bind to a variety of proteins bearing cross-reactive epitopes, it may be disadvantageous to use antibodies raised against a cell surface antigen that is a member of a conserved gene family or that contains a conserved sequence present in many other cell surface proteins. Further, immunoglobulins that bind cell surface proteins may be inefficiently endocytosed and/or may cause premature disruption of the immunoliopsome upon binding antigen thereby releasing the exogenous DNA from the immunoliposome prior to fusion (Ho and Huang, J. Immunol. 134:4035 (1985)). In addition, immunoliposome-DNA preparations can be relatively inefficient for transfection.

Behr et al, Proc. Natl. Acad. Sci. USA 86:6982 (1989) reported using lipopolyamine as a reagent to mediate transfection, without the necessity of any additional phospholipid to form liposomes. Lipopolyamines, however, do not impart a predetermined targeting specificity to the exogenous DNA; cells can be transfected indiscriminately.

Low molecular weight polylysine ("PL") and other polycations are carriers that can be used to effect DNA-mediated transfection into cells. Zhou et al, Biochem. Biophys. Acta 1065:8 (1991) have reported synthesis of a polylysine-phospholipid conjugate, a lipopolylysine comprising PL linked to N-glutarylphosphatidylethanolamine, which reportedly increases the transfection efficiency of DNA as compared to lipofectin, a commercially used transfection reagent. A lipopolylysine may not, however, provide satisfactory cell type specificity and transformation efficiency.

Polylysine molecules conjugated to asialoorosomucoid ("ASOR") (Wu and Wu, J. Biol. Chem. 262:4429 (1987); Wu and Wu, Biochemistry 27:887 (1988); Wu and Wu, J. Biol. Chem. 263:14621 (1988); Wu and Wu, J. Biol. Chem. 267:12436 (1992); Wu et al, J. Biol. Chem. 266:14338 (1991); and Wilson et al, J. Biol. Chem. 267:963 (1992), WO 92/06180; WO 92/05250; and WO 91/17761) or transferrin (Wagner et al, Proc. Natl. Acad. Sci. USA 87:3410 (1990); Zenke et al, Proc. Natl. Acad. Sci. USA 87:3655 (1990); Birnstiel WO 92/13570) have been described. Such conjugates, which may be particularly useful when liver is the target tissue, can be expected to provide target-specific delivery of associated DNA of the invention to cells that express the appropriate receptor (ie, asialoglycoprotein receptor or transferrin receptor). WO 91/14696 describes covalently bound conjugates consisting of oligonucleotides in disulfide linkage to a targeting agent that promotes transport across cell membranes for transferring short antisense oligonucleotides into cells. Birnstiel, WO 91/17773, describes polycation conjugates comprising an anti-CD4 antibody or a HIV gp120 fragment to confer targeting specificity for CD4+ T cells. Similar methods can be used to specifically deliver DNA of the invention to cancer cells (eg cells of HCC or breast tumors) expressing a cell surface receptor that can be targeted with a ligand or a specific antibody reactive with the receptor (eg a mutated form of the MGP/IGF-II receptor), CEA, etc. These methods increase the specificity of delivering the exogenous polynucleotides to a particular cell type, however, they may have a relatively low transfection efficiency.

Liposome mediated transfection is highly efficient and generally not cell type specific, and lipid:DNA complexes rapidly associate with cells of the reticuloendothelial system (Mannino and Gould-Fogerite, BioTech 6:682 (1988)). Receptor-mediated transfection should allow any size DNA or RNA to be transfected, however, efficiency can be affected by lysosomal degradation of nucleic acid. Accordingly, the use of inhibitors of lysosomal degradation (lysosomotropic agents), which are usually administered essentially contemporaneously, may be advantageous. Cytotoxicity of many of these agents (like chloroquine) may, however, limit the universal employment of receptor mediated transfection (Dean et al, Biochem. J. 217:27 (1984)).

Essentially, any suitable DNA delivery method can be used in the context of the present invention, although direct physical application of naked DNA comprising the expression construct/transgene to the target-cell population (eg, HCC or breast tumor mass) may be preferred.

The nucleic acid-containing compositions of the invention can be stored and administered in a sterile physiologically acceptable carrier, where the nucleic acid is dispersed in conjunction with any agents which aid in the introduction of the DNA into cells.

Various sterile solutions may be used for administration of the composition, including water, PBS, ethanol, lipids, etc. The concentration of the DNA will be sufficient to provide a therapeutic dose, which will depend on the efficiency of transport into the cells.

Actual delivery of the gene sequence, formulated as described above, can be carried out by a variety of techniques including direct injection, instillation of lung and other epithelial surfaces, intravenous injection and other physical methods (including microprojectiles to target visible and accessible regions of tissue (eg with naked DNA)

—lithotriptic shock can be used to focus on specific body regions and render them receptive to DNA uptake). Administration may be by syringe needle, trocar, cannula, catheter, etc, as a bolus, a plurality of doses or extended infusion, etc. The dose may be administered intralesionally, intravascularly or other appropriate site.

Naked DNA has been shown to be taken up relatively efficiently in certain tissues (especially muscle). Direct injection of viruses or liposomes can thus be used alone or in combination with systemic delivery. Similarly, instillation of lung and other epithelial surfaces can be used to localize the tumor suppressive gene sequence. This approach can be used in combination with systemic delivery in the case of disseminated disease. The suppressor gene sequences of the invention administered by intravenous injection can be targeted by using specific expression control sequences (eg those for surfactant protein A (SPA) for lung, CEA for colorectal, PSA for prostate and alphafetoprotein (AFP) for liver or mutant forms of the M6P/IGF-II receptor).

The compositions containing the present receptor sequences can be administered for prophylactic and/or therapeutic treatments. In therapeutic application, compositions are administered to a patient already affected by the particular neoplastic/hypertrophic disease (eg HCC or breast tumor), in an amount sufficient to cure or at least partially arrest the condition and its complications. An amount adequate to accomplish this is defined as a "therapeutically effective dose" or "efficacious dose". Amounts effective for this use will depend upon the severity of the condition, the general state of the patient, and the route of administration.

In addition to gene therapy, the present invention also contemplates site directed chemotherapy using antibodies or fragments (eg F(ab')$_2$ fragments) thereof (advantageously, human or humanized monoclonal) or oligonucleotides specific for mutant forms of the M6P/IGF-II receptor. In accordance with this approach, antibodies or oligonucleotides conjugated, directly or indirectly, with an appropropriate toxin or radionucleotide are administered (eg by intravenous injection) to a subject under conditions such that the toxin or radionucleotide accumulates at the tumor site and destroys the tumor cells or inhibits their replication. (See Ghetie and Vitetta, Recent Current Opinion in Immunology 6:707 (1994); Bachier and LeMaistre, Clin. Immunother. 3:450 (1995)). Alternatively, antibody could be coupled to an enzyme (eg cytosine deaminase) capable of converting a prodrug into a cytotoxic drug at the site of the tumor (eg cytosine deaminase can convert 5-fluorocytosine to 5-fluorouracil) (see, for example, WO 88/07378, WO 95/13095 and U.S. Pat. No. 4,975,278).

Risk Assessment:

The demonstration that the M6P/IGF-II receptor gene functions as a tumor suppressor gene and that its loss occurs early in tumorigenesis indicates that it can be used in human carcinogen risk assessment studies, for example, studies based on rodent carcinogenesis studies. Since the M6P/IGF-II receptor gene is imprinted in rodents (ie monoallelic expression), but is not imprinted in most humans (ie biallelic expression), rodents can be expected to be more sensitive than humans to those carcinogens in which the M6P/IGF-II receptor gene is mechanistically involved in the etiology of tumor formation.

The diagnostic, therapeutic and risk assessment methodologies described herein are applicable to both humans and non-human mammals.

Certain aspects of the invention will be described in greater detail in the non-limiting Example that follows.

EXAMPLE I

METHODOLOGY

RT PCR analysis:

First strand cDNA synthesis was performed as follows: 50 mM Tris.HCl, pH 8.3, 75 mM KCl, 3 mM MgCl$_2$, 10 mM DTT, 0.5 mM 4dNTP mix, 1 $\mu$M reverse primer (see below), 2–5 $\mu$g total RNA, and 200 units M-MLV reverse transcriptase (GIBCO BRL, Gaithersburg, Md.) in a total volume of 20 $\mu$l. RNA and H$_2$O were mixed and heated to 65° C. for 10 min and then chilled on ice prior to the addition of the other ingredients. The final mixture was incubated at 37° C. for 60 min and then at 65° C. for 10 min. After one extraction with a mixture of phenol:chloroform:isoamyl alcohol (25:24:1 (v/v) respectively), excess reverse primer was removed using a CHROMA SPIN-100 DEPC gel filtration column. 1 $\mu$l of the eluate was used in PCR as follows: 10 mM Tris.HCl, pH 8.3 (at 25° C.), 50 mM KCl, 1 mM MgCl$_2$, 200 $\mu$M 4dNTP mix, 200 nM forward and reverse primers (see below), 1 $\mu$l RT template, and 2.5 units Taq DNA polymerase (Perkin Elmer Corporation, Norwalk, Conn.) in a total volume of 100 $\mu$l. Hot-start PCR was carried out under the following conditions: 1 min denaturing at 94° C., 1 min annealing at 55° C., and 1 min extension at 72° C. for 35 cycles with an additional 5 min extension for cycle 35 on a DNA Thermal Cycler (Perkin Elmer Corporation, Norwalk, Conn.). Because the fidelity of Taq DNA polymerase is such that errors can be introduced during the PCR process, a number of precautions were taken to address this potential problem. Mutant templates were amplified in two or more independent PCRs and templates were generated from both RNA and genomic DNA. In all cases, the corresponding surrounding normal template was amplified in parallel with the tumor template, and the tumor mutations were confirmed by direct sequencing in both directions.

MISMATCH DETECT™ assay:

Sequence differences between normal and tumor cDNA templates were identified according to the manufacturers instructions (Ambion Inc., Austin, Tex.). Utilizing the T7 and SP6 phage promoters, both forward and reverse transcripts were synthesized, respectively, from the normal and tumor cDNA templates. The normal T7 transcript was hybridized to tumor SP6 transcript and visa versa. Hybridization of T7 and SP6 transcripts from normal cDNA provided a control. Following RNase A digestion, the products were analyzed on an agarose gel. Mismatches were identified either by the appearance of new bands or an increase in band intensity relative to that in the control.

Identification of the C:G→A:T transversion:

The following primers were used in RT PCR. RT primer was M6P-7166R (GAACTTCTCCTACAGCAAGTGG) (SEQ ID NO:1). First round primers were M6P-6092F (AAACAAAAGTTGTCTGCCCTCC) (SEQ ID NO:2) and M6P-7143R (CAGCTTACTTATCACTGTTTCC) (SEQ ID NO:3). The UT, LT and normal bands were gel purified prior to second round amplification with T7-M6P-6108F (GATAATACGACTCACTATAGGGCCCTCCAAAGAA-GTTGGAGTGC) (SEQ ID NO:4) and SP6-M6P-6639R (TCATTTAGGTGACACTATAGGAGTAGTTGTCCCCA-TTGGTCCTC) (SEQ ID NO:5). Sequence changes between normal and tumor cDNA templates were identified using Ambion's MISMATCH DETECT™ assay. PCR products were directly sequenced using the AMPLICYCLE™ kit (Perkin Elmer, Norwalk, Conn.) and the above primers. Genomic DNA was amplified using M6P-6092F and M6P-6301R (GTCCCAGGACCTGGACGTCACC) (SEQ ID NO:6). Following gel purification of this DNA fragment, direct sequencing was done using M6P-IntronF (TGTGACTGTTCCTGGAAGCAGC) (SEQ ID NO:7) and M6P-IntronR (CAGGTTCTTCCAGCTCCAGAGG) (SEQ ID NO:8).

Identification of the G:C→T:A transversion and the G:C→A:T transition:

The following primers were used in RT PCR. RT primer was M6P-5231R (CGTGCATGGGATTTAGTGGCTGAC) (SEQ ID NO:9). First round primers were M6P-3812F (TGGAAGGGGACAACTGTGAGG) (SEQ ID NO:10) and M6P-5141R (ACCACCAGTGCGATGAATAAGGG) (SEQ ID NO:11). Second round primers were T7-M6P-4269F (GATAATACGACTCACTATAGGGCTGGCAACTCCTT- CGACCTC) (SEQ ID NO:12) and SP6-M6P-5136R (TCATTTAGGTGACACTATAGGACAGTGCGATGAAT- AAGGGGAGAC) (SEQ ID NO:13). Genomic DNA was amplified using the primer pair M6P-4401F (GCCGTGCCCTCCAGAAGCAGCC) (SEQ ID NO:14) and M6P-4569R (CACTTGGCTCTCGCTGCAGGTG) (SEQ ID NO:15). PCR templates were directly sequenced using M6P-4411F (CCAGAAGCAGCCGCGTGTCTGC) (SEQ ID NO:16) and M6P-4559R (TCGCTGCAGGTGAATCGGATGG) (SEQ ID NO:17).

RNase protection assay:

The RNase protection assay was performed as previously described (Sue et al, Ann. Surg. 222:171 (1995)). An antisense riboprobe was prepared as follows. Using normal human genomic DNA as template, first round PCR was carried out with the primers M6P-6092F (AAACAAAAGTTGTCTGCCCTCC) (SEQ ID NO:18) and M6P-6301R (GTCCCAGGACCTGGACGTCACC) (SEQ ID NO:19). Second round PCR was, carried out using T7-M6P-6108F (GATAAT ACGACTCACT- ATAGGGCCCTCCAAAGAAGTTGGAGTGC) (SEQ ID NO:20) and SP6-INTRON-R2 (TCATTTAGGT- GACAC- TATAGGACAGTCCGCCCAGGTTCT TCCAG) (SEQ ID NO:21). Using the second round PCR product as a template and utilizing the SP6 promoter, a 395 bp antisense riboprobe (flanking 107 bp of the 3' end of exon 40 and 263 bp of the 5' end of intron 40) was synthesized and used in the assay.

Immunohistochemical staining for the M6P/IGF-II receptor:

Frozen sections, 6 μm in thickness, were fixed in 100% ethanol and immunoperoxidase stained with diaminobenzidine according to the methods of Jirtle et al (Carcinogenesis 15:1473 (1994)). All sections were immunohistochemically stained in an identical manner at the same time. In all cases, rabbit IgG antibody was used as a negative control on serial sections. The sections were counterstained with haematoxylin.

RESULTS

Figure 5:
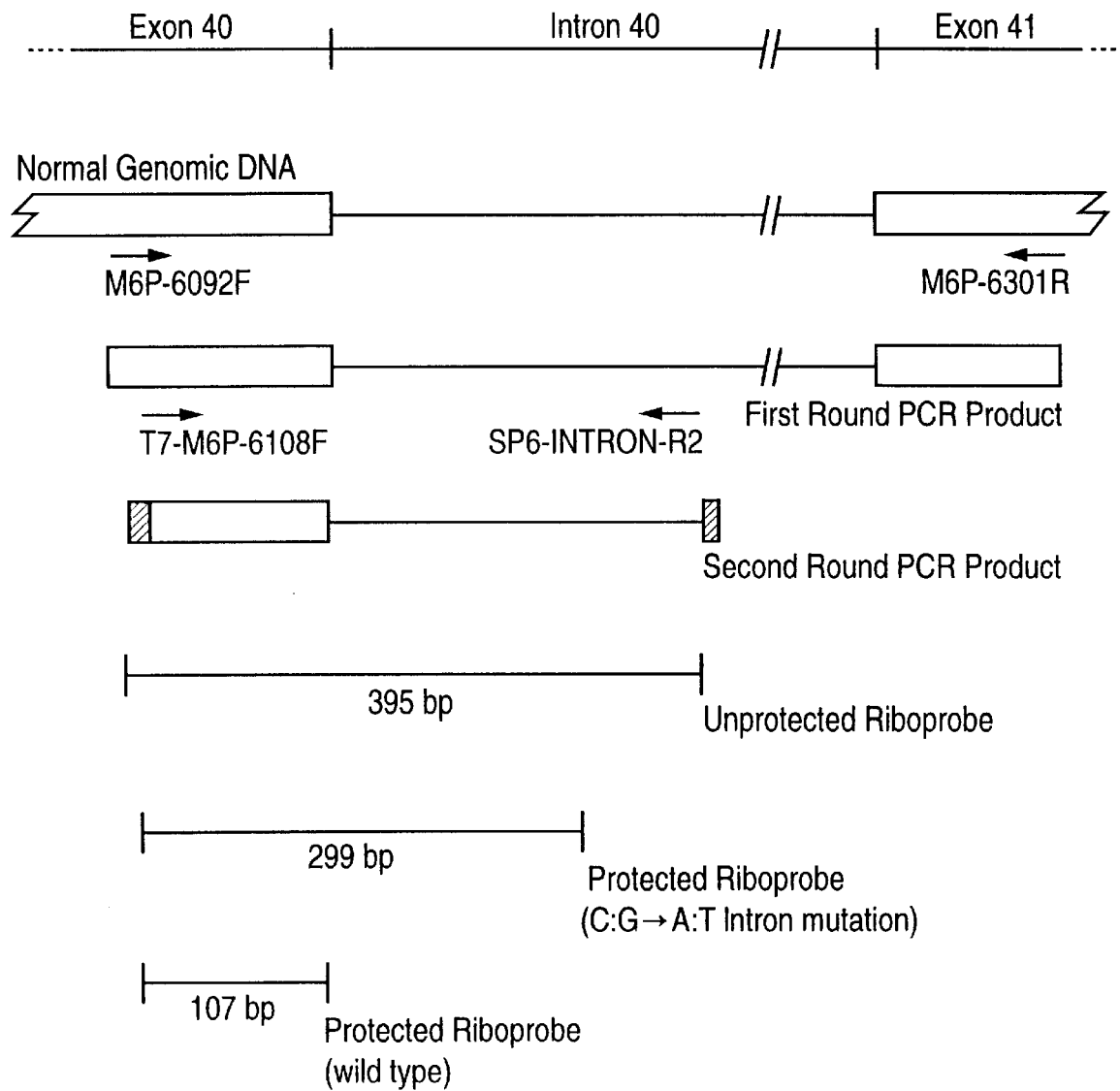
FIG. 5 Preparation of riboprobe and expected size of the protected fragments. Open boxes represent exons and the horizontal line intron 40. Black boxes represent the T7 and SP6 promoters, respectively. Arrows represent primers as indicated. The size of the protected fragments is given in base pairs (bp).
Figure 6:
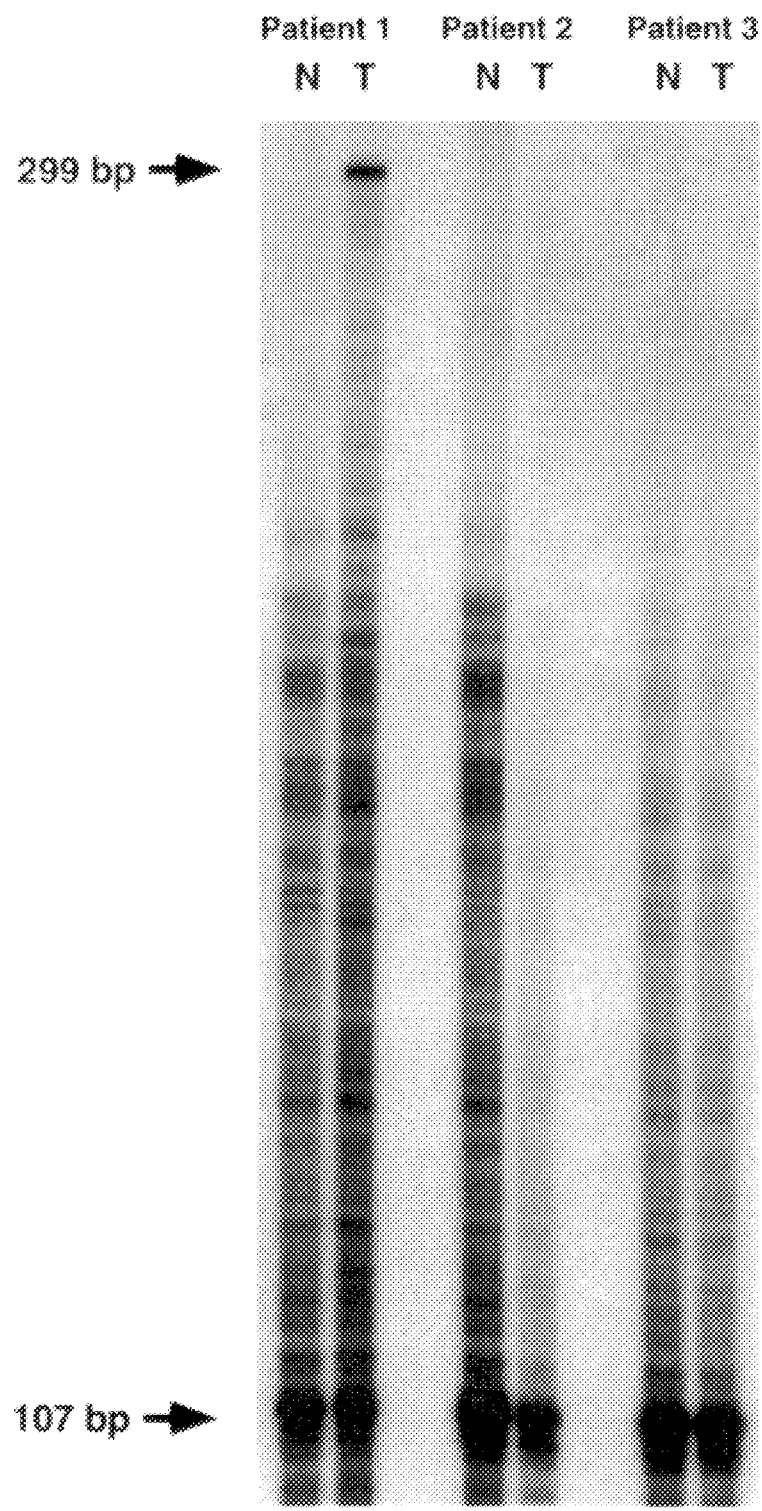
FIG. 6 RNase protection assay for the product of the C:G→A:T transversion mutant on normal (N) and tumor (T) RNA from the three patients each with HCCs. N, surrounding normal; T, tumor. Protected fragments are indicated by arrows. Patient 1: tumor has the C:G→A:T intron mutation, patients 2 and 3: tumors do not have the C:G→A:T intron mutation.
Figure 8A:
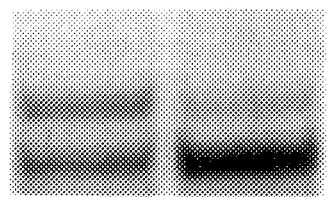
FIGS. 8A–F Representative non-informative and informative patients with and without LOH at the M6P/IGF-II receptor locus in breast tumors. N, normal tissue; T, tumor tissue. A–B, informative invasive carcinoma patients with LOH; C–D, informative carcinoma in situ patients with LOH; E, informative invasive carcinoma patient without LOH; F, non-informative invasive carcinoma patient.
Figure 8B:
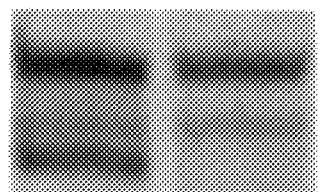
Figure 8C:
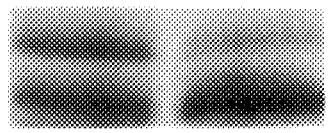
Figure 8D:
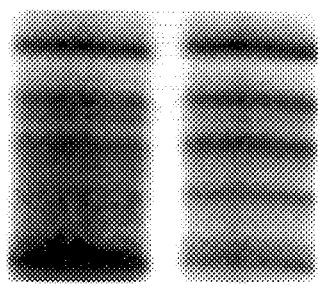
Figure 8E:
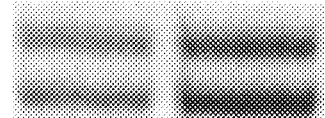
Figure 8F:

Seventy percent of human hepatocellular tumors have LOH at the M6P/IGF-II receptor locus (De Souza et al, Oncogene 10:1725 (1995)) which maps to 6q26–q27 (Laureys et al, Genomics 3:224 (1988)). Using total RNA from human HCCs exhibiting LOH at the M6P/IGF-II receptor locus (De Souza et al, Oncogene 10:1725 (1995)), the remaining allele was screened for mutations using Ambion's MISMATCH DETECT™ assay. In one HCC, reverse transcription polymerase chain reaction (RT-PCR) amplification of the region flanked by the primers M6P-6092 Forward and M6P-7143Reverse produced one band with normal template and two bands with tumor template (FIG. 2A). The lower tumor (LT) band migrated with the normal band whereas the upper tumor (UT) band was approximately 200 base pairs (bp) larger suggesting a possible insertion. When the gel purified normal, UT and LT bands were reamplified and used as templates for mismatch detection, the UT band produced two cleavage products suggesting a mismatch whereas the LT band was indistinguishable from the normal control (FIG. 2B). Direct sequencing of the UT band revealed a 192 bp insert in the M6P/IGF-II receptor message (FIG. 2C). The presence of this insert was confirmed using an RNase protection assay. (See FIGS. 5 and 6).

The corresponding region on genomic DNA from normal and tumor templates was amplified. The expected amplicon size for this region was 230 bp and 422 bp for normal and mutant tumor cDNA templates, respectively. However, an amplicon of ≈1200 bp was observed, suggesting an insert size of ≈970 bp. Direct sequencing revealed that the insert observed in tumor cDNA was the 5' end of an intron that corresponds to intron 40 in mice (FIG. 3A) (Szebenyi et al, Genomics 19:120 (1994)). Furthermore, a comparison of the homology between the normal and tumor intron sequences revealed a C:G→A:T point mutation in the tumor (FIG. 3A and FIG. 3B).

The C:G→A:T transversion observed in tumor genomic DNA appears to create an alternative 5' splice site within this intron (FIG. 3A, box B) the sequence of which is more closely related to the consensus sequence (AGGTAAGT) for 5' splice sites than the normally used 5' splice site (FIG. 3A, box A) .(Horowitz et al, Trends Genet. 10:100 (1994); Padgett et al, Ann. Rev. Biochem. 55:1119 (1986)). Therefore, the 5' end of this intron becomes incorporated into the M6P/IGF-II receptor message (FIG. 2C and FIG. 3C) causing a dramatic effect on translation since the first codon after that for $Ser^{2023}$ becomes the stop codon, TGA (FIG. 2C and FIG. 3C). Truncation of the M6P/IGF-II receptor protein at this position prevents synthesis of both the transmembrane domain and the lysosomal trafficking signals of this receptor (Kornfeld, Ann. Rev. Biochem. 61:307 (1992)). This results not only in the secretion of the mutant M6P/IGF-II receptor but also of lysosomal enzymes (Wang et al, Nature 372:464 (1994)).

Figure 4A:
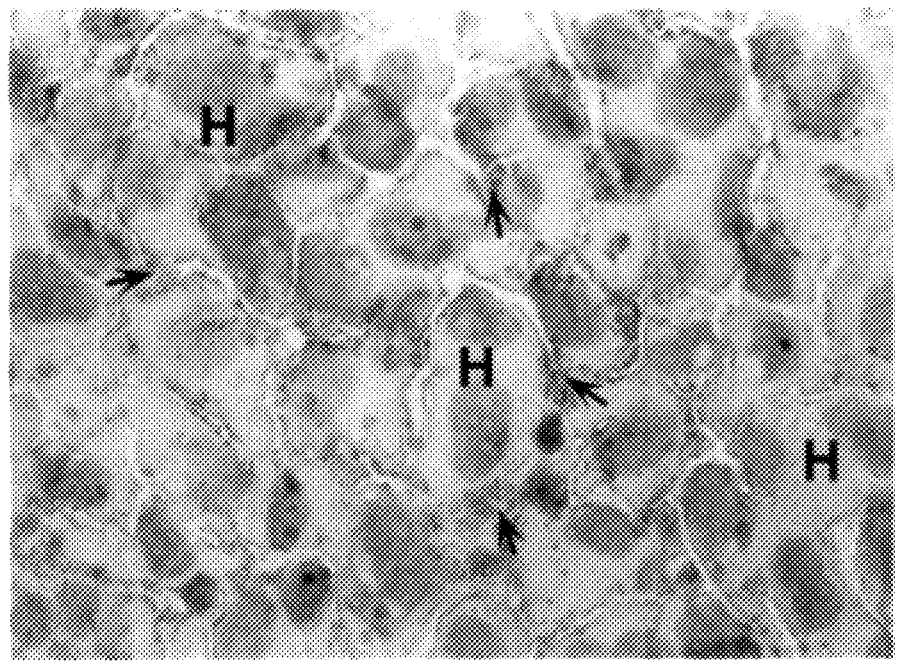
FIGS. 4A–B Immunohistochemical staining for the M6P/IGF-II receptor. (A)—M6P/IGF-II receptor staining in the HCC with LOH and containing the C:G→A:T intron mutation. As predicted by this intron mutation, the M6P/IGF-II receptors are present primarily in the extracellular spaces (arrows). In contrast, the hepatocellular tumor cells (H) contain very low to no detectable receptors. Magnification, X630. (B)—M6P/IGF-II receptor staining in a HCC without LOH and lacking the C:G→A:T intron mutation. Strong intracellular staining for the M6P/IGF2-II receptor is present in the hepatocellular tumor cells (H). The stromal elements are marked by an (S). Magnification, X630. Serial sections were unstained when non-immune rabbit IgG was used instead of the primary antibody.
Figure 4B:
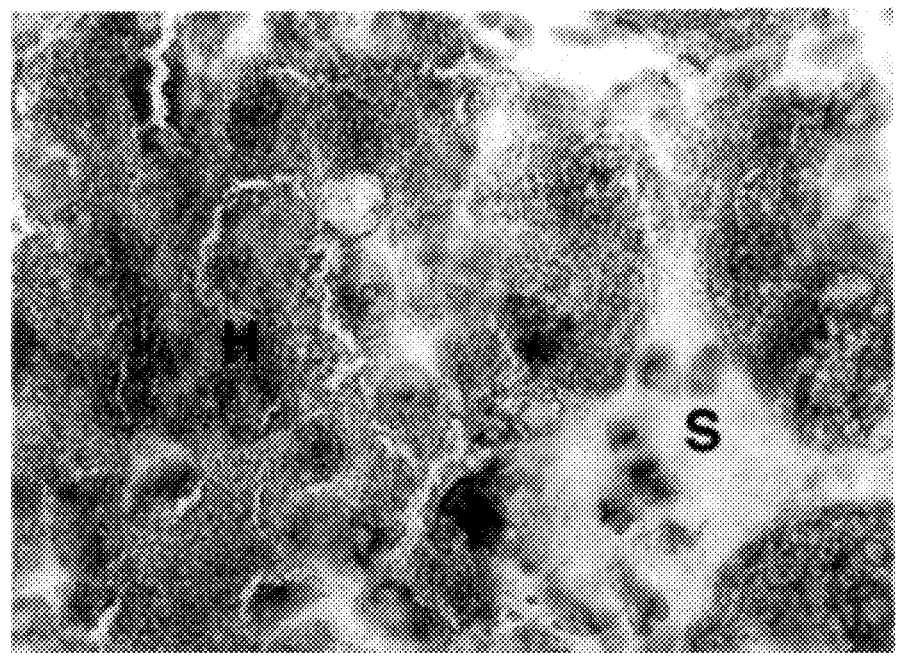

Immunohistochemical staining of this HCC was performed using a polyclonal antibody against the M6P/IGF-II receptor protein (FIG. 4A) (Hartshorn et al, J. Endochrinol. 121:221 (1988)). As predicted from the C:G→A:T intron mutation, the primary staining for the M6P/IGF-II receptor was observed only extracellularly. In contrast, in an HCC without LOH and lacking this C:G→A:T transversion, strong intracellular staining for the M6P/IGF-II receptor was observed (FIG. 4B) consistent with the observation that normally 90% of the receptors are within the cell (Kornfeld, Ann. Rev. Biochem. 61:307 (1992)). A second identical C:G→A:T intron mutation was also observed in a HCC without LOH.

A G:C→T:A transversion was also identified in a second .hepatocellular carcinoma with LOH (FIG. 7A and FIG. 7B). This mutation, which is in a region corresponding to exon 31 of the mouse gene (Szebenyi et al, Genomics 19:120 (1994)), results in the substitution of Val for $Gly^{1449}$ in the protein (FIG. 7D). Using the Chou-Fasman algorithm for protein secondary structure determination (MacDNASIS® Pro v3.2, Hitachi Software Engineering America, Ltd.), this amino acid alteration is predicted to increase β-sheeting. Additionally, $Gly^{1449}$ is conserved among human, bovine, rat and mouse (FIG. 7D) providing further support for a significant functional role for this amino acid. A second identical G:C→T:A transversion was observed in a HCC without LOH. Further analysis of this region revealed a third mutation, a G:C→A:T transition in an HCC with LOH (FIG. 7C). The G:C→A:T transition results in the substitution of Glu for Gly$^{1464}$ (FIG. 7D), and appears to alter protein secondary structure by decreasing β-sheeting. The M6P/IGF-II receptor contains 15 repeat domains; repeats 1 to 3 and 6 to 9 have been implicated in the binding of M6P residues (Westlund et al, J. Biol. Chem., 266:23233 (1991); Dahms et al, J. Biol. Chem. 268:5457 (1993)) and repeat 11 in the binding of IGF-II (Dahms et al, J. Biol. Chem. 269:3802 (1994), Schmidt et al, J. Biol. Chem. 270:14975 (1995)). Both the G:C→T:A transversion and the G:C→A:T transition are located in repeat 10, a region closely associated with ligand binding.

EXAMPLE II

MATERIALS AND METHODS

Patients

Frozen tissues (n=38) or paraffin embedded tissue sections (n=24) from 62 patients with histopathologically confirmed (RC Bentley) breast tumors were obtained from the Department of Surgery and the Department of Pathology, Duke University Medical Center. All patients were treated between 1989 and 1994.

DNA and RNA Isolation

For those patients in which frozen tissue was available, both high molecular weight DNA and total RNA were extracted from histologically confirmed breast tumor and DNA was extracted from the autologous peripheral blood lymphocytes. DNA was extracted as previously described (Miller et al, Nucleic Acids Res. 16:1215 (1988)). Cells were lysed in 20 mM Tris-Hcl, pH8.0; 10 mM EDTA; 0.5% SDS; 100 mM NaCl; 10 mg/ml proteinase K at 55° C. overnight. The lysate was extracted with phenol and chloroform, ethanol precipitated, then the DNA pellet was rinsed in 700 ethanol, dried and resuspended in TE buffer, pH 8.0. RNA was extracted using TRIZOL (GIBCO-BRL, Gaithersburg, Md.) (Chomczynski et al, Anal. Biochem. 162:156 (1987)).

Tissue Microdissection from Paraffin Embedded Sections

Microdissection of tumor and surrounding normal breast tissue from 10 μm histology sections was performed by previously described methods (Hedrum et al, Biotech 7:118 (1994); De Souza et al, Oncogene 10:1725 (1995)). Briefly, paraffin embedded sections were deparaffinized in xylene (2× 5 minutes), washed in 100% ethanol (2× 5 minutes) and 50% ethanol (2× 5 minutes), and rehydrated in $H_2O$ prior to staining. Tissue sections were stained for 30 sec with 2% (w/v) methylene blue and then rinsed in $H_2O$ and allowed to air dry. Tumor (>50 cells) and surrounding normal tissue were then dissected and put in 50 μl of 1× PCR buffer (10 mM Tris.HCl, pH 8.3 (at 25° C.), 50 mM KCl) containing 2 μl 20 mg/ml proteinase K (Boehringer Mannheim, Indianapolis, Ind.). The mixture was incubated at 56° C. for 60 min and then at 100° C. for 10 min. 5 μl of this mixture were used in the PCR analysis described below.

PCR Analysis for LOH

Two nucleotide repeats polymorphisms have been observed in the 3' untranslated region of the human M6P/IGFIIr gene. There is a tetranucleotide (Hol et al, Hum. Mol. Genet. 1:347 (1992)) repeat close to a dinucleotide repeat (Goto et al, Nucleic Acids Res. 20:923 (1992)) which together give observed heterozygosity of 58% (Hol et al, Hum. Mol. Genet. 1:347 (1992)). These polymorphisms were used to investigate the frequency of LOH at the M6P/IGF-II receptor locus in patients with breast tumors using PCR. To assess whether the whole end of 6q was deleted, LOH at D6S281 (Weissenbach et al, Nature 359:794 (1992)) was looked for using a primer pair from Research Genetics, Inc. (Huntsville, Ala.). The reaction conditions for PCR were as follows: 10 mM Tris.HCl, pH 8.3 (at 25° C.), 50 mM KCl, 1 mM $MgCl_2$, 200 μM 4dNTP mix, 200 nM forward and reverse primers (Hol et al, Hum. Mol. Genet. 1:347 (1992)), 5 μl microdissected template, and 2.5 units Taq DNA polymerase (Perkin Elmer Corporation, Norwalk, Conn.) in a total volume of 100 μl. Hot-start PCR was carried out under the following conditions: 1 min denaturing at 94° C., 1 min annealing at 55° C., and 1 min extension at 72° C. for 30 cycles with an additional 5 min extension for cycle 30 on a DNA Thermal Cycler (Perkin Elmer Corporation, Norwal, Conn.). The DNA generated by PCR was characterized by agarose gel electrophoresis and dideoxy sequencing (Sanger et al, Proc. Natl. Acad. Sci. USA 74:5463 (1987)), the sequences corresponded to those expected.

Excess primers were removed using a CHROMA SPIN-100 DEPC gel filtration column (CLONTECH, Palo Alto, Calif.). 5 μl of the eluate was then end-labeled with [γ-$^{33}$P] ATP (2000 Ci/mmol, 10 mCi/ml) (DuPont NEN, Boston, Mass.) using 10 units T4 polynucleotide kinase (Boehringer Mannheim, Indianapolis, Ind.) and 1× phosphorylation buffer from the manufacturer in a total volume of 20 μl. The mixture was incubated at 37° C. for 30 min and then at 90° C. for 5 min. Sequencing gel-loading buffer (95% (v/v) deionized formamide, 20 mM EDTA, pH 8.0, 0.05% (w/v) xylene cyanol FF, and 0.05% (w/v) bromophenol blue) was added to the labeled PCR products in a ratio of 1:1 prior to heat denaturation (80° C. for 3 min) and electrophoresis on a 6% denaturing polyacrylamide sequencing gel. The electrophoretic products were visualized by autoradiography.

Because contaminating normal tissue can make it difficult to detect LOH in tumors, allelic loss in informative (heterozygous) patients was defined as a >50% decrease in the ratio of the two alleles in the tumor versus that in the surrounding normal tissue. Alleles were scored as previously described for PCR amplified dinucleotide repeats (Louis et al, Am. J. Path. 141:777 (1992)).

RT PCR Amplification

First strand cDNA synthesis was performed as follows: 50 mM Tris.HCl, pH 8.3, 75 mM KCl, 3 mM $MgCl_2$, 10 mM DTT, 0.5 mM 4dNTP mix, 1 μM reverse primer (see below), 2–5 μg total RNA, and 200 units SUPERSCRIPT reverse transcriptase (GIBCO BRL, Gaithersburg, Md.) in a total volume of 20 μl. RNA and $H_2O$ were mixed and heated to 65° C. for 10 min and then chilled on ice prior to the addition of the other ingredients. The final mixture was incubated at 37° C. for 60 min and then at 65° C. for 10 min. After one extraction with a mixture of phenol:chloroform:isoamyl alcohol (25:24:1 (v/v) respectively), excess reverse primer was removed using a CHROMA SPIN-100 DEPC gel filtration column; 1 μl of the eluate was used in PCR amplification as outlined above.

Direct Sequencing of PCR Products

Because the fidelity of Taq DNA polymerase is such that errors can be introduced during the PCR process, a number of precautions were taken to address this potential problem. Mutant templates were amplfed in two or more independent PCRs. In all cases the corresponding normal template was amplified in parallel with the tumor template, and the tumor mutations were confirmed by direct sequencing in both directions. In each case, genomic DNA was amplified using an outer primer pair, primers were removed using a CHROMA SPIN-100 gel filtration column (CLONTECH, Palo Alto, Calif.) and 1 μl product used in a second round amplification using an inner primer pair. Depending on the cleanness of the second round on an agarose gel, primers were removed from the second round products as before or the appropriate band was gel purified. The second round products were directly sequenced using the AmpliCycle™ kit (Perkin Elmer, Norwalk, Conn.) and the second round primers. Primer pairs were as follows:
Identification of Exon 31 Mutations:
 Outer primer pair: hM6P-4401F (GCCGTGCCCTCCAGAAGCAGCC) (SEQ ID NO:22) and hM6P-4569 R(CACTTGGCTCTCGCTGCAGGTG) (SEQ ID NO:23). Inner primer pair: hM6P-4411F (CCAGAAGCAGCCGCGTGTCTGC) (SEQ ID NO:24) and hM6P-4559R (TCGCTGCAGGTGAATCGGATGG) (SEQ ID NO:25).
Identification of Exon 48 (Cytoplasmic Domain) Mutations:
 Outer primer pair: hM6P-7214F (GTGAATAAGGAAGAAGAGACAG) (SEQ ID NO:26) and hM6P-7686R (TTATTTGGTTGGAGGTGCTTGG) (SEQ ID NO:27). Three overlapping inner primer pairs were used: hM6p-7214F (GTGAATAAGGAAGAAGAGACAG) (SEQ ID NO:28) and hM6P-7453R (CACTGGGTGGGAGCTCTCTGCC) (SEQ ID NO:29), hM6P-7361F (GATGACCAGGACAGTGAGGATGAG) (SEQ ID NO:30) and hM6P-7536R (TTCCCTTTCCTCGCCTTCTCAC) (SEQ ID NO:31), and hM6P-7446F (ACCCAGTGAGAAACGCACAGAG) (SEQ ID NO:32) and hM6P-7686R (TTATTTGGTTGGAGGTGCTTGG) (SEQ ID NO:33).

RESULTS

Using the polymerase chain reaction (PCR), 62 patients with breast tumors were screened for LOH at the M6P/IGF-II receptor locus; 38 were invasive carcinomas and 24 were carcinomas in situ (CIS) (Table 1 and FIG. 8). Of these, 40 (65%) were informative (heterozygous) for a polymorphic dinucleotide repeat sequence and a tetranucleotide deletion/insertion polymorphism located in the 3' untranslated region of the receptor (Hol et al, Human Mol. Genet. 1:347 (1992); Goto et al, Nucleic Acids Res. 20:923 (1992)). This frequency is consistent with the 58% heterozygosity previously reported for these polymorphisms (Hol et al, Human Mol. Genet. 1:347 (1992)). LOH at the M6P/IGF-II receptor locus was observed in 12/40 (30%) informative patients while only 3/26 (12%) informative patients showed LOH at the more distal locus, D6S281, a percentage well within the typical allelic imbalance background range.

TABLE 1

Loss of heterozygosity at the M6P/IGFIIr locus in human breast tumors

| Breast Tumor Type (n) | Informative (I) vs. Non-Informative (NI) | LOH in Informative Patients |
| --- | --- | --- |
| Invasive Carcinoma (38) | 21 (I) | 7/21 (33%) |
|  | 17 (NI) | — |
| Carcinoma In Situ (CIS) (24) | 19 (I) | 5/19 (26%) |
|  | 5 (NI) | — |
| Total (62) | 40 (I) | 12/40 (30%) |
|  | 22 (NI) |  |

In the majority of informative patients, the two M6P/IGF-II receptor alleles differed by only two base pairs. The PCR amplification of dinucleotide repeats is known to produce slippage bands below the true allele (Louis et al, Am. J. Path. 141:777 (1992)) and these slippage bands would tend to mask the loss of allele 2 but not of allele 1. Furthermore, the presence of contaminating normal tissue in tumors would obscure the loss of either allele. Although microdissection of tumor reduces this problem, all tumors contain normal connective tissue and inflammatory cells which have the constitutive genotype (Louis et al, Am. J. Path. 141:777 (1992)). Such contaminiation is evident as a faint band in those informative patients exhibiting LOH (FIG. 8). As a consequence, the total frequency of LOH reported may be an underestimation of the true value.

Within the 40 breast tumors in informative patients, 21 were invasive carcinomas and 19 were carcinomas in situ. LOH at the M6P/IGF-II receptor locus occurred in 7/21 (33%) invasive carcinomas, 4/14 (29%) comedo CIS, and the only papillary CIS, but in none of the non-comedo or lobular CIS (Table 2). Comedo CIS, which is characterized by necrosis in the involved spaces, appears more phenotypically malignant than other CIS (Morrow et al, Diseases of the Breast, (1996), Harris et al (eds). Lippincott-Raven, Philadelphia, Pa., pp. 355–373). Although the numbers of non-comedo and lobular tumors were small, the occurance of LOH and mutations (below) in the high grade (comedo) CIS tumors, but not in the non-comedo and lobular CIS tumors is provocative. The observation of LOH in carcinomas in situ and similar rates of LOH in comedo CIS and invasive carcinoma indicate that allelic loss may be an early event in the etiology of some breast cancers.

TABLE 2

Loss of heterozygosity at the M6P/IGFIIr locus in breast carcinomas in situ.

| Carcinoma in situ Type (n) | Informative (I) vs. Non-Informative (NI) | LOH in Informative Patients |
| --- | --- | --- |
| Comedo DCIS (18) | 14 (I) | 4/14 (29%) |
|  | 4 (NI) | — |
| Non-Comedo DCIS & Lobular CIS (5) | 4 (I) | 0/4 (0%) |
|  | 1 (NI) | 1/1 (100%) |
| Papillary CIS (1) | 0 (NI) | — |
| Total | 19 (I) | 5/19 (26%) |
| Carcinoma In Situ (CIS) (24) | 5 (NI) | — |

Part of the M6P/IGF-II receptor gene was examined for mutations using direct sequencing of PCR products (Meltzer, PCR Protocols: Current Methods and Applications, White, BA (ed) Humana Press: Totowa, N.J., pp. 137–141 (1993)) and missense mutations were found in three of the twelve tumors showing LOH. The mutations were found in one invasive carcinoma and two comedo carcinomas in situ. These mutations were found in regions of the gene which may be involved in ligand binding and in trafficking of lysosomal proteins.

Figure 9A:
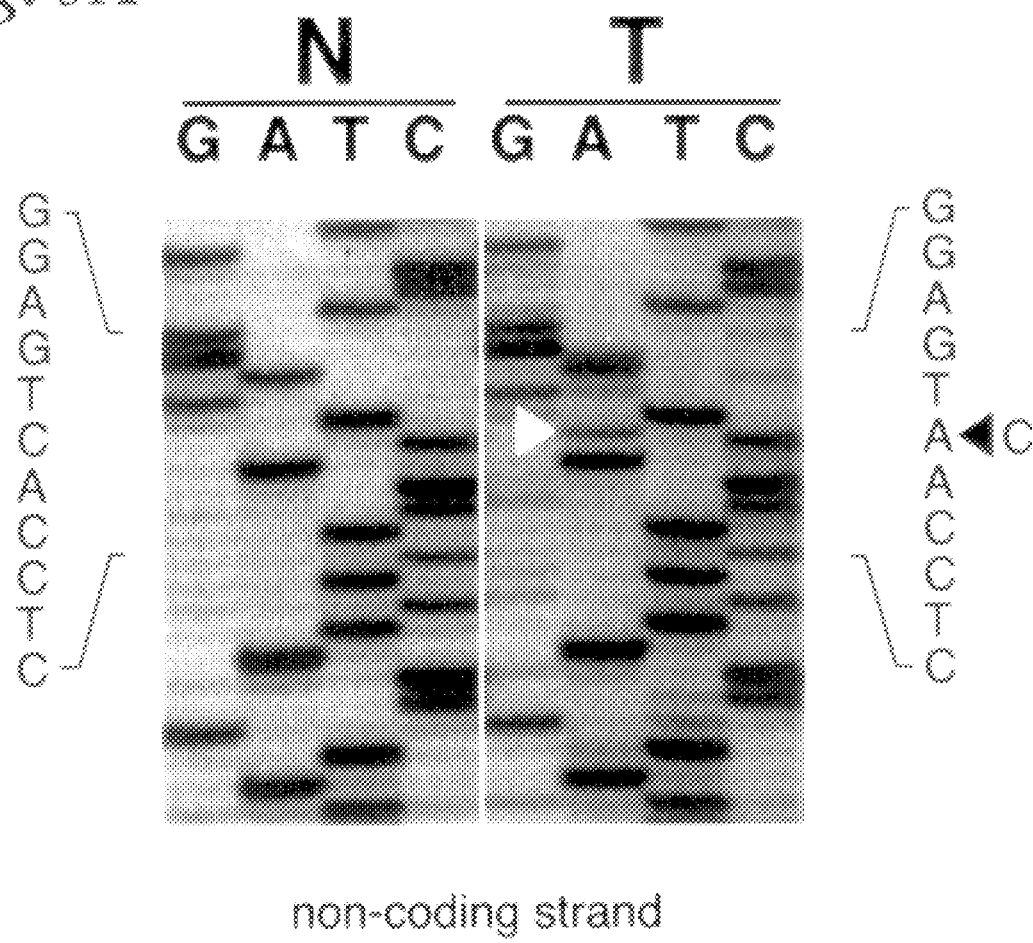

A G:C→T:A transversion was identified in a comedo carcinoma in situ with LOH. This mutation results in the substitution of His for $Gln^{1445}$ in the protein (FIG. 9), a substitution of a basic residue for an uncharged one. This mutation is in a region corresponding to exon 31 of the mouse gene (Szebenyi et al, Genomics 19:120 (1994)) which codes for part of repeat 10, a region closely associated with ligand binding. The M6P/IGF-II receptor contains 15 repeat domains; repeats 3 and 9 have been implicated in the binding of MGP residues (Westlund et al, J. Biol. Chem. 266:23233 (1991), Dahms et al, J. Biol. Chem. 269:3802 (1993)) and repeat 11 in the binding of IGF2 (Dahms et al, J. Biol. Chem. 269:3802 (1994); Schmidt et al, J. Biol. Chem. 270:14975 (1995)). This substitution is only four residues away from one observed in HCCs.

Three additional mutations in two tumors were identified in the coding region of exon 48 (based on the mouse sequence, Szebenyi et al, Rotwein, Genomics 19:120

(1994)). This exon codes for most of the cytoplasmic domain of the M6P/IGF-II receptor. A major function of the M6P/IGF2 is thought to be related to the sorting of newly synthesized lysosomal enzymes and the endocytosis of extracellular phosphorylated lysosomal enzymes and IGF2 (Dahms et al, J. Biol. Chem. 264:12115 (1989)). One mutation, ea C:G→A:T transversion in a comedo carcinoma in situ, results in the substitution of Thr for Pro$^{2379}$ (FIGS. 10A and B) 23 residues downstream from the receptor internalization signal. The Chou-Fasman-Rose algorithm for protein secondary structure determination (MacDNASIS® Pro v3.2, Hitachi Software Engineering America, Ltd.) predicts this substitution will create an additional region of beta sheeting in the protein. This proline is conserved in the M6P/IGF-II receptor in all species sequenced to date, and is also present in a conserved domain found in MARCKS family proteins and MRP (FIG. 10; Blackshear et al,.J. Biol. Chem. 267:13540 (1992), Blackshear, J. Biol. Chem. 268:1501 (1993)), however, the function of this domain is unknown. The other two mutations in exon 48 are a G:C→A:T transition and a T:A→A:T transversion in an invasive carcinoma. These mutations result in the substitution of an Asn for Ser$^{2400}$ and a Thr for Ser$^{2401}$ which are predicted to change part of an alpha helical region to beta sheeting based on the Chou-Fasman-Rose algorithm.

All documents cited above are hereby incorporated in their entirety by reference.

One skilled in the art will appreciate from a reading of this disclosure that various changes in form and detail can be made without departing from the true scope of the invention.

What is claimed is:

1. A method of detecting neoplastic or preneoplastic cells in a cell or tissue sample comprising screening DNA present in said sample for loss of heterozygosity at 6q26–q27 and for a mutation in the M6P/IGF-II receptor gene, the presence of said loss of heterozygosity at 6q26–q27 and said mutation being indicative of the presence of said neoplastic or preneoplastic cells.

2. The method of claim 1 wherein said sample is derived from the blood, lung, ovary, prostate, bladder, pancreas, gastrointestinal tract, liver or breast of a mammal.

3. The method according to claim 2 wherein the sample is derived from the lung, liver, breast or gastrointestinal tract of said mammal.

4. The method according to claim 1 wherein the mutation results in a truncation or loss of the encoded M6P/IGF-II receptor.

5. The method according to claim 4 wherein the encoded M6P/IGF-II receptor lacks the transmembrane and lysosomal trafficking signal.

6. The method according to claim 1 wherein the mutation is a point mutation.

7. The method according to claim 1 wherein the mutation is a deletion.

8. The method according to claim 7 wherein the deletion is in a minimicrosatellite region comprising an eight polydeoxyguanosine track spanning nucleotides 4089 to 4096 of the M6P/IGF-II receptor gene.

9. The method according to claim 1 wherein the point mutation results in an amino acid substitution in the encoded M6P/IGF-II receptor.

10. The method according to claim 9 wherein the point mutation results in a C:G→A:T transversion, a G:C→T:A transversion, a G:C→A:T transition, a T:A→A:T transversion, or a G:C→C:G transversion.

11. The method according to claim 10 wherein the point mutation results in a G:C→T:A transversion that results in the substitution of Val for Gly$^{1449}$ of the M6P/IGF-II receptor.

12. The method according to claim 10 wherein the point mutation results in a G:C→A:T transition that results in the substitution of Glu for Gly$^{1464}$ of the M6P/IGF-II receptor.

13. The method according to claim 10 wherein the point mutation results in a G:C→T:A transversion that results in the substitution of His for Gln$^{1445}$.

14. The method according to claim 10 wherein the point mutation results in a C:G→A:T transversion that results in the substitution of Thr for Pro$^{2379}$.

15. The method according to claim 10 wherein the point mutation results in a G:C→A:T transition that results in substitution of Asn for Ser$^{2400}$.

16. The method according to claim 10 wherein the point mutation results in a T:A→A:T transversion that results in substitution of Thr for Ser$^{2401}$.

17. The method according to claim 10 wherein the point mutation results in a G:C→C:G transversion that results in substitution of Cys for Ser$^{1262}$.

18. A method of detecting preneoplastic cells in a cell or tissue sample comprising screening DNA present in said sample for a mutation in the M6P/IGF-II receptor gene, the presence of said mutation being indicative of the presence of said preneoplastic cells.

19. The method of claim 18 wherein said sample is derived from the blood, lung, ovary, prostate, bladder, pancreas, gastrointestinal tract, liver or breast of a mammal.

20. The method according to claim 19 wherein the sample is derived from the lung, liver, breast or gastrointestinal tract of said mammal.

* * * * *